United States Patent
Stern et al.

(10) Patent No.: US 9,630,177 B2
(45) Date of Patent: Apr. 25, 2017

(54) MICROFLUIDIC DEVICES, SYSTEMS AND METHODS FOR SAMPLE PREPARATION AND ANALYSIS

(71) Applicant: GENAPSYS, INC., Redwood City, CA (US)

(72) Inventors: Seth Stern, Palo Alto, CA (US); Hesaam Esfandyarpour, Redwood City, CA (US); David Eberhart, Santa Clara, CA (US)

(73) Assignee: GenapSys, Inc., Redwood City, CA (US)

( * ) Notice: Subject to any disclaimer, the term of this patent is extended or adjusted under 35 U.S.C. 154(b) by 0 days.

(21) Appl. No.: 14/656,028

(22) Filed: Mar. 12, 2015

(65) Prior Publication Data

US 2015/0258544 A1    Sep. 17, 2015

Related U.S. Application Data

(60) Provisional application No. 61/952,829, filed on Mar. 13, 2014.

(51) Int. Cl.
*B01L 3/00* (2006.01)
*F16K 3/00* (2006.01)
(Continued)

(52) U.S. Cl.
CPC ...... *B01L 3/502738* (2013.01); *B01F 3/0865* (2013.01); *B01F 5/0206* (2013.01);
(Continued)

(58) Field of Classification Search
CPC .... B01L 3/00; B01L 99/00; F16K 3/00; A61J 1/06; G01N 21/00
(Continued)

(56) References Cited

U.S. PATENT DOCUMENTS 7,790,118 B2 * 9/2010 Maltezos et al. ............. 422/129
7,814,928 B2 * 10/2010 Maltezos et al. ............. 137/340
(Continued)

FOREIGN PATENT DOCUMENTS

WO   WO 2012/047889 A2   4/2012
WO   WO 2012/166742 A2  12/2012
(Continued)

OTHER PUBLICATIONS

International search report and written opinion dated Jun. 3, 2015 for PCT/US2015/020130.
(Continued)

*Primary Examiner* — Brian J Sines
(74) *Attorney, Agent, or Firm* — Snell & Wilmer L.L.P.

(57) ABSTRACT

The present disclosure provides microfluidic devices, systems and methods for sample preparation and/or analysis. A microfluidic device can include a first channel having a sequence of (n) chambers each having a first volume (v). The first channel can include one or more valves at opposing ends of the first channel that fluidically isolate the first channel. The microfluidic device can further include a second channel in fluid communication with the first channel. The second channel can include at least one second chamber having a total second volume that is at least equal to the total volume of the first channel (n*v). The second channel can include one or more valves at opposing ends of the second channel that fluidically isolate the second channel from the first channel.

6 Claims, 37 Drawing Sheets

(51) Int. Cl.

| | | |
|---|---|---|
| *A61J 1/06* | (2006.01) | |
| *G01N 21/00* | (2006.01) | |
| *B01L 99/00* | (2010.01) | |
| *C12N 15/10* | (2006.01) | |
| *B01L 7/00* | (2006.01) | |
| *B01F 5/02* | (2006.01) | |
| *B01F 13/00* | (2006.01) | |
| *B01F 3/08* | (2006.01) | |
| *F16K 99/00* | (2006.01) | |

(52) U.S. Cl.
CPC ...... *B01F 13/0059* (2013.01); *B01L 3/50273* (2013.01); *B01L 7/525* (2013.01); *C12N 15/1013* (2013.01); *F16K 99/0015* (2013.01); *F16K 99/0059* (2013.01); *B01L 2200/0668* (2013.01); *B01L 2200/0684* (2013.01); *B01L 2300/0636* (2013.01); *B01L 2300/0645* (2013.01); *B01L 2300/087* (2013.01); *B01L 2300/0816* (2013.01); *B01L 2300/0864* (2013.01); *B01L 2300/0867* (2013.01); *B01L 2300/0877* (2013.01); *B01L 2300/0887* (2013.01); *B01L 2300/123* (2013.01); *B01L 2300/1822* (2013.01); *B01L 2400/0481* (2013.01); *B01L 2400/0655* (2013.01); *F16K 2099/008* (2013.01); *F16K 2099/0084* (2013.01)

(58) Field of Classification Search
USPC .............. 422/502, 503, 504, 509, 537, 554; 436/43, 180
See application file for complete search history.

(56) References Cited

U.S. PATENT DOCUMENTS

| | | |
|---|---|---|
| 8,584,703 B2 | 11/2013 | Kobrin et al. |
| 2004/0209354 A1 | 10/2004 | Mathies et al. |
| 2008/0142157 A1* | 6/2008 | Maltezos et al. ............. 156/300 |
| 2010/0165784 A1 | 7/2010 | Jovanovich et al. |
| 2012/0138460 A1 | 6/2012 | Baghbani-Parizi et al. |
| 2013/0034880 A1 | 2/2013 | Oldham |

FOREIGN PATENT DOCUMENTS

| | | |
|---|---|---|
| WO | WO 2013/082619 A1 | 6/2013 |
| WO | WO 2014/152625 A1 | 9/2014 |
| WO | PCT/US2014/069624 | 12/2014 |

OTHER PUBLICATIONS

Kricheldorf, et al. Thermoplastic Elastomers. 3rd Edition, Hanser Verlag, 2004.

* cited by examiner

MICROFLUIDIC DEVICES, SYSTEMS AND METHODS FOR SAMPLE PREPARATION AND ANALYSIS

CROSS-REFERENCE

This application claims the benefit of U.S. Provisional Patent Application No. 61/952,829, filed Mar. 13, 2014, which is entirely incorporated herein by reference.

BACKGROUND

The goal to elucidate the entire human genome has created interest in technologies for rapid deoxyribonucleic acid (DNA) sequencing, both for small and large-scale applications. Important parameters are sequencing speed, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed and long read lengths, may provide the necessary measurement capability.

Nucleic acid sequencing is a process that can be used to provide sequence information for a nucleic acid sample. Such sequence information may be helpful in diagnosing and/or treating a subject. For example, the nucleic acid sequence of a subject may be used to identify, diagnose and potentially develop treatments for genetic diseases. As another example, research into pathogens may lead to treatment for contagious diseases.

There are methods available, which may be used to sequence a nucleic acid. Such methods, however, are expensive and may not provide sequence information within a time period and at an accuracy that may be necessary to diagnose and/or treat a subject.

SUMMARY

Sample preparation for nucleic acid sequencing can utilize clonal amplification and may involve two stages or more stages, including nucleic acid purification followed by library preparation. Methods for nucleic acid purification are highly diverse, reflecting the diversity of nucleic acid sources (e.g., blood, fresh tissue, preserved formalin-fixed paraffin-embedded tissue, aspirates, swabs, cultured cells, or environmental samples). Methods for library preparation from purified nucleic acids are also diverse, reflecting the diversity of nucleic sequencing applications (e.g., whole genome sequencing, targeted exome sequencing, or mRNA sequencing). These complex procedures are typically performed manually by highly trained scientists and technicians working at laboratory benches. This is partly due to the automation of these procedures requiring the use of liquid-handling laboratory robots, which are large, expensive, and difficult to program. As sequencing costs have rapidly declined, the cost of sample preparation has become a significant factor in the overall cost of sequencing projects. There is therefore an increasing need for cost-effective automation of sample preparation. The present disclosure provides methods and devices that can be used for sample preparation that utilize microfluidics.

An aspect of the disclosure provides a microfluidic device. The microfluidic device can comprise a first channel having a sequence of (n) chambers each having a first volume (v). The first channel can comprise valves at opposing ends of the first channel that fluidically isolate the first channel. Moreover, the microfluidic device can further comprise a second channel in fluid communication with the first channel. The second channel can include at least one second chamber having a total second volume that is at least equal to the total volume of the first channel (n*v). Additionally, the second channel can comprise valves at opposing ends of the second channel that fluidically isolate the second channel from the first channel.

In some embodiments, the microfluidic device can further comprise a third channel in fluid communication with the first channel and the second channel. The third channel can include at least one third chamber having a total third volume that is at least equal to a sum of the first and second channel volumes (2n*v). In some embodiments, at least two of the first channel, second channel and third channel may be substantially parallel to one another. In some embodiments, the first channel and second channel can be substantially parallel to one another.

In some embodiments, the microfluidic device can further comprise at least a fluidic layer, an actuation layer, and an elastic layer sandwiched between the fluidic layer and the actuation layer. In some embodiments, the elastic layer may be formed of a thermoplastic elastomer. In some embodiments, the elastic layer may be substantially free of polydimethylsiloxane.

In some embodiments, at least one of the valves may comprise a diaphragm in the elastic layer; a valve seat that selectively isolates an inlet and an outlet of the at least one of the valves; and a chamber in the actuation layer. The chamber can supply positive or negative pressure to move the diaphragm towards or away from the valve seat. In some embodiments, the diaphragm may be deformable and actuatable. In some embodiments, the at least one of the valves may further comprises a pin that is movable within the chamber relative to the diaphragm. The diaphragm may be movable towards the valve seat using positive pressure at least partly supplied by the pin. In some embodiments, the diaphragm may be movable towards the valve seat with positive pressure supplied by the pin and positive fluid pressure supplied by the actuation layer.

In some embodiments, at least one of the chambers may comprise a diaphragm in the elastic layer; a fluid chamber in the fluidic layer; and a chamber in the actuation layer. The chamber can supply positive or negative pressure to deform the diaphragm to effect fluid flow or mixing in fluid chamber. In some embodiments, the at least one of the chambers may further comprise a pin that is movable within the chamber relative to the diaphragm. The diaphragm can be movable using positive pressure at least partly supplied by the pin. In some embodiments, the diaphragm may be movable using positive pressure supplied by the pin and positive fluid pressure supplied by the actuation layer.

In some embodiments, a first subset of the n chambers in the first channel may be in thermal communication with a first temperature zone and/or a second subset of the n chambers in the first channel may be in thermal communication with a second temperature zone. In some embodiments, the first temperature zone and second temperature zone may be different temperature zones. In some embodiments, the first temperature zone and the second temperature zone may be independently controllable. In some embodiments, a third subset of the n chambers in the first channel may be in thermal communication with a third temperature zone.

In some embodiments, n may be equal to at least 1, 2, 3, 4, 5, 6, 7, 8, 9, 10, 11, 12, 13, 14, 15, 16 or more. In some embodiments, n may be equal to at least 3. In some embodiments, n may be equal to at least 6. In some embodiments, the first channel and second channel may be isolatable from one another with the aid of the valves at opposing ends of the first channel and the second channel. In some embodiments, the microfluidic device may further comprise a plurality of wells that are in selective fluid communication with the first channel and the second channel. At least a subset of the plurality of wells can be for holding reagent(s) for biological sample preparation or analysis. In some embodiments, the total second volume may be substantially equal to the total volume of the first channel.

An additional aspect of the disclosure provides a system for sample preparation or analysis. The system can comprise a microfluidic device that comprises a first channel having a sequence of (n) chambers each having a first volume (v). The first channel can comprise valves at opposing ends of the first channel that fluidically isolate the first channel. The microfluidic device can further comprise a second channel in fluid communication with the first channel. The second channel can include at least one second chamber having a total second volume that is at least equal to a total volume of the first channel (n*v). Moreover, the second channel can comprise valves at opposing ends of the second channel that fluidically isolate the second channel from the first channel. Additionally, the system can further comprise a controller that is programmed to actuate the valves at the opposing ends of the first channel and the second channel to regulate fluid flow through the first channel and the second channel.

In some embodiments, the microfluidic device may further comprise a third channel in fluid communication with the first channel and the second channel. The third channel can include at least one third chamber having a total third volume that is at least equal to a sum of the first and second channel volumes (2n*v). In some embodiments, at least two of the first channel, second channel and third channel may be substantially parallel to one another. In some embodiments, the first channel and second channel can be substantially parallel to one another.

In some embodiments, the microfluidic device can comprise at least a fluidic layer, an actuation layer, and an elastic layer sandwiched between the fluidic layer and the actuation layer. In some embodiments, the elastic layer can be formed of a thermoplastic elastomer. In some embodiments, the elastic layer can be substantially free of polydimethylsiloxane. In some embodiments, at least one of the valves may comprise a diaphragm in the elastic layer; a valve seat that selectively isolates an inlet and an outlet of the at least one of the valves; and a chamber in the actuation layer. The chamber can supply positive or negative pressure to move the diaphragm towards or away from the valve seat. In some embodiments, the diaphragm can be deformable and actuatable. In some embodiments, at least one of the valves can further comprise a pin that is movable within the chamber relative to the diaphragm. The diaphragm can be movable towards the valve seat using positive pressure at least partly supplied by the pin.

In some embodiments, at least one of the chambers may comprise a diaphragm in the elastic layer; a fluid chamber in the fluidic layer; and a chamber in the actuation layer. The chamber can supply positive or negative pressure to deform the diaphragm to effect fluid flow or mixing in fluid chamber. In some embodiments, the at least one of the chambers may further comprise a pin that is movable within the chamber relative to the diaphragm. The diaphragm can be movable using positive pressure at least partly supplied by the pin. In some embodiments, the diaphragm may be movable using positive pressure supplied by the pin and positive fluid pressure supplied by the actuation layer.

In some embodiments, a first subset of the n chambers in the first channel is in thermal communication with a first temperature zone and/or a second subset of the n chambers in the first channel is in thermal communication with a second temperature zone. In some embodiments, the first temperature zone and second temperature zone may be different temperature zones. In some embodiments, the first temperature zone and second temperature zone can be independently controllable. In some embodiments, a third subset of the n chambers in the first channel may be in thermal communication with a third temperature zone.

In some embodiments, n may be equal to at least 1, 2, 3, 4, 5, 6, 8, 9, 10, 11, 12, 13, 14, 15, 16 or more. In some embodiments, n may be equal to at least 3. In some embodiments, n may be equal to at least 6. In some embodiments, the first channel and second channel may be isolatable from one another with the aid of the valves at opposing ends of the first channel and the second channel.

In some embodiments, the microfluidic device may further comprise a plurality of wells that are in selective fluid communication with the first channel and the second channel. At least a subset of the plurality of wells can be for holding reagent(s) for biological sample preparation or analysis. In some embodiments, the total second volume may be substantially equal to the total volume of the first channel.

In some embodiments, the system may further comprise a sensor array in fluid communication with the microfluidic device. The sensor array can comprise individual sensors that detect signals that are indicative of a reaction or reaction product(s) associated with the sample or derivative thereof. In some embodiments, the individual sensors may each include at least two electrodes that are in a Debye layer of a bead having the sample or derivative thereof during sensing, where the at least two electrodes detect the signals. In some embodiments, the signals may correspond to an impedance associated with the sample or the bead. In some embodiments, the controller may be programmed to direct a flow of the sample or derivative thereof from the microfluidic device to the sensor array, and facilitate detection of the signals that are indicative of the reaction or reaction products(s).

An additional aspect of the disclosure provides a microfluidic device. The microfluidic device can comprise a fluid layer having a fluid chamber in fluid communication with a fluid inlet and a fluid outlet; an actuation layer having a pin that is movable in the actuation layer; and a diaphragm between the fluid layer and the actuation layer. The diaphragm can be formed of a thermoplastic elastomer and/or can be deformable in the fluid chamber upon application of positive pressure to the diaphragm. The positive pressure can be supplied by a combination of the pin moving towards the diaphragm and positive fluid pressure in the actuation layer.

In some embodiments, the diaphragm may be substantially free of polydimethylsiloxane. In some embodiments, the pin may be uniaxially movable in the actuation layer. In some embodiments, the positive pressure may be supplied by the pin contacting the diaphragm and moving towards the diaphragm. In some embodiments, the microfluidic device may further comprise a valve seat in the fluid layer. The diaphragm can be actuatable to contact the valve seat upon the application of the positive pressure to the diaphragm. Contact can fluidically isolate the fluid inlet from the fluid outlet.

An additional aspect of the disclosure provides a system comprising a plurality of microfluidic devices. An individual microfluidic device of the plurality of microfluidic devices can comprise a fluid layer having a fluid chamber in fluid communication with a fluid inlet and a fluid outlet; an actuation layer having a pin that is movable in the actuation layer; and a diaphragm between the fluid layer and the actuation layer. The diaphragm can be formed of a thermoplastic elastomer and/or the diaphragm can be deformable in the fluid chamber upon application of positive pressure to the diaphragm. Positive pressure can be supplied by a combination of the pin moving towards the diaphragm and positive fluid pressure in the actuation layer.

An additional aspect of the disclosure provides a method for biological sample preparation or analysis. The method can comprise providing microfluidic device having a first channel having a sequence of (n) chambers each having a first volume (v). The first channel can comprise valves at opposing ends of the first channel that fluidically isolate the first channel. Moreover, the microfluidic device can have a second channel in fluid communication with the first channel. The second channel can include at least one second chamber having a total second volume that is at least equal to the total volume of the first channel (n*v). The second channel can comprise valves at opposing ends of the second channel that fluidically isolate the second channel from the first channel. The method can further comprise directing flow of the biological sample or derivative thereof among the n chambers of the first channel; from the first channel to the second channel; or from the second channel to the first channel.

In some embodiments, the microfluidic device may further comprise a third channel in fluid communication with the first channel and the second channel. The third channel can include at least one third chamber having a total third volume that is at least equal to a sum of the first and second channel volumes (2n*v). In some embodiments, directing the flow of the biological sample or derivative thereof can further comprise directing flow of the biological sample or derivative thereof from the first channel or second channel to the third channel, or vice versa.

In some embodiments, the method may further comprise directing flow of the biological sample or derivative thereof from the microfluidic device to a sensor array in fluid communication with the microfluidic device. The sensor array may comprise individual sensors that detect signals that are indicative of a reaction or reaction product(s) associated with the sample or derivative thereof. In some embodiments, the method further comprises using the individual sensors to detect the signals that are indicative of a reaction or reaction product(s) associated with the biological sample or derivative thereof. In some embodiments, the signals may correspond to an impedance associated with the biological sample or a bead coupled to the biological sample during detection of the signals.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGS." herein), of which:

DETAILED DESCRIPTION

Figure 1:
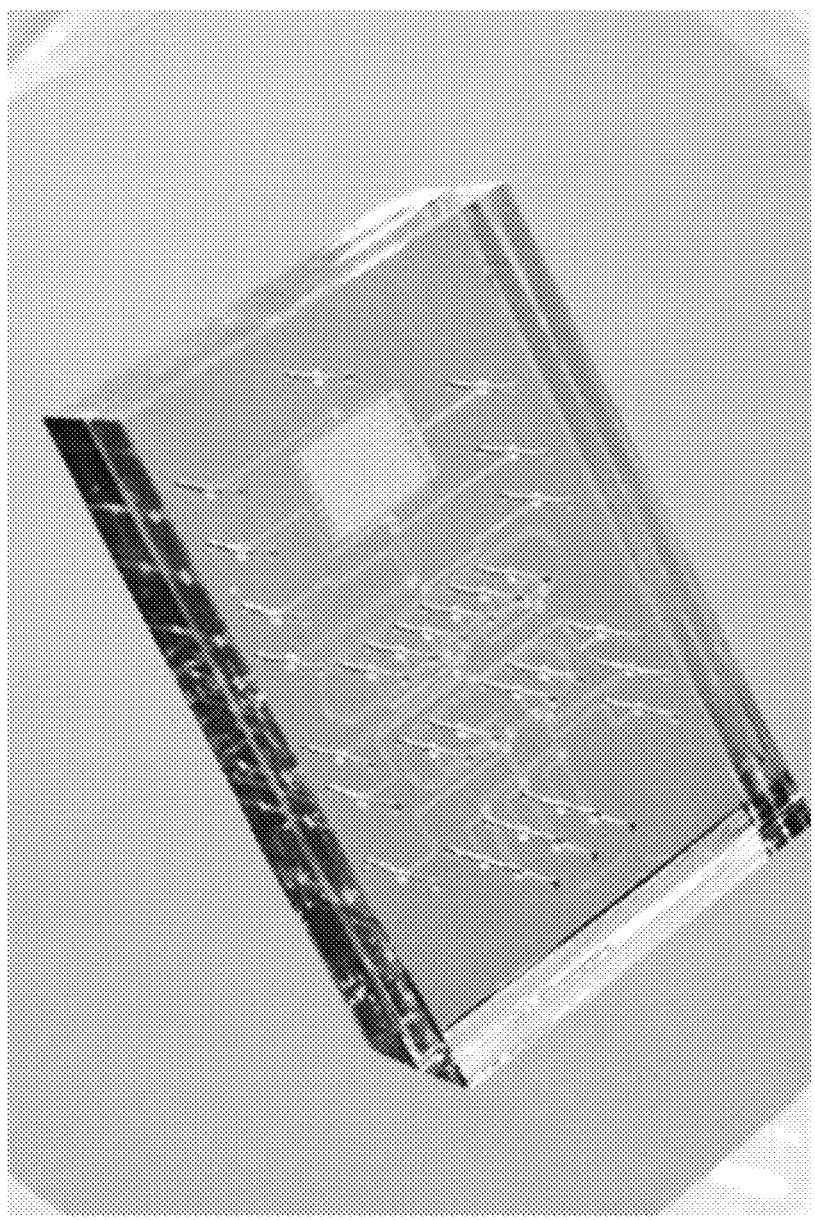
FIG. 1 is a photograph of a Multilayer Soft Lithography (MSL) Digital Pneumatic Microfluidic (DPM) device of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As described herein, microfluidic devices can provide a useful alternative to laboratory robots for sample preparation as microfluidic devices reduce reaction sizes and reagent consumption while also automating these procedures. However, while numerous microfluidic technologies have been developed, the successful commercialization of microfluidic systems is rare. Some current microfluidic systems require casting of multiple layers of a liquid polydimethylsiloxane (PDMS) prepolymer, a relatively expensive process compared with injection molding or hot embossing. PDMS is itself expensive compared with alternative thermoplastic and thermoplastic elastomer materials. Moreover, PDMS is highly permeable to gases, water, and small water-soluble molecules. This means that pumps and valves for such devices may need to be hydraulically actuated (with water or oil) rather than actuated with air. In many cases, these devices are incompatible with certain chemistries, or may be surface treated to be useful. Together, these characteristics increase the cost of microfluidic devices while also significantly complicating their use.

Other microfluidic technologies suffer from similar high fabrication costs and/or user barriers that limit their utility. Consequently, there remains a need for a low-cost, versatile, and convenient-to-use microfluidic technology.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules.

The term "nucleic acid," as used herein, generally refers to a molecule comprising one or more nucleic acid subunits. A nucleic acid can be deoxyribonucleic acid (DNA), ribonucleic acid (RNA), or variants thereof. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polymeric form of nucleotides that may have various lengths, either deoxyribonucleotides (DNA) or ribonucleotides (RNA), or analogs thereof. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may include one or more non-standard nucleotide(s), nucleotide analog(s) and/or modified nucleotides.

The term "reagent," as used herein, generally refers to one or more substances that can be employed for use sample preparation or analysis. Sample preparation can include sample processing. An example of sample preparation is a nucleic acid amplification reaction, such as polymerase chain reaction (PCR). Examples of reagents for use with nucleic acid amplification reactions include one or more primers and a polymerase, as well as cofactors (e.g., magnesium or manganese).

The term "polymerase,' as used herein, generally refers to any enzyme capable of catalyzing a polymerization reaction. Examples of polymerases include, without limitation, a nucleic acid polymerase. A polymerase can be a polymerization enzyme. In some cases, a transcriptase or a ligase is used (i.e., enzymes which catalyze the formation of a bond).

Digital Pneumatic Microfluidic Devices

The present disclosure provides microfluidic devices that may be employed for use in biological sample preparation and/or analysis. Systems of the present disclosure may be used upstream of a biological and/or chemical sensing system, such as a sensor chip as described elsewhere herein. The sensing may be integrated with a microfluidic device, such as on the same cartridge, or may be separate from the microfluidic device. The sensing system can be used for sensing various biological species or biological and/or chemical reactions. For instance, the sensing system can sense nucleic acids, proteins, antigens and antibodies. The sensing system can include one or more individual sensors and may be situated downstream of the microfluidic device. The sensing system may be as described elsewhere herein, and/or as in PCT Patent Application No. PCT/US2011/054769, PCT Patent Application No. PCT/US2012/039880, PCT Patent Application No. PCT/US2012/067645, PCT Patent Application No. PCT/US2014/027544, PCT Patent Application No. PCT/US2014/069624 and U.S. patent application Ser. No. 13/481,858, each of which is incorporated herein by reference in its entirety for all purposes.

The present disclosure provides various advantages over conventional microfluidic chip technology, including, without limitation, (i) superior, low-cost elastomers for on-chip pneumatic membrane pumps and valves, (ii) low-cost, high-volume chip fabrication methods, (iii) pre-configured on-board reagents, and (iv) a digital architecture that flexibly processes discrete volumes. Combined together, these materials, methods, and designs can produce low-cost, low-user-burden, highly functional microfluidic chips that are capable of single-step mixing of components, cascading any number of consecutive operations, incubating reactions at temperatures between about 4° C. and about 100° C., thermocycling, and processing magnetic beads for nucleic acid purification. These devices can permit cost-effective and workflow-effective utilization of microfluidic technology in multiple biomedical applications, including diverse sample and library preparation methods for sequencing technologies.

FIG. 1 shows an example of a Multilayer Soft Lithography (MSL) device of the present disclosure, which can perform cell lysis, nucleic acid (e.g., DNA) purification and nucleic acid amplification (e.g., PCR). This device can be used to process various types of samples, such as a blood sample. For example, this device may be used to perform nucleic acid amplification from blood.

Figure 2:
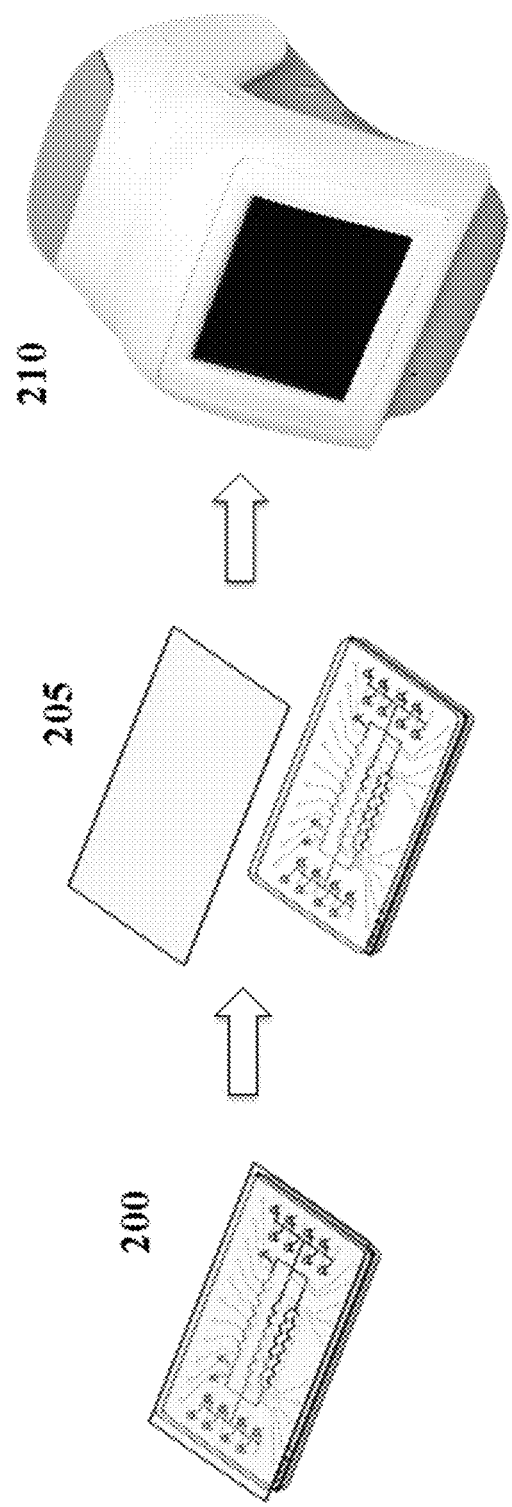
FIG. 2 schematically illustrates a DPM system.

The present disclosure provides a compact, cost-effective and workflow-effective Digital Pneumatic Microfluidic (DPM) chip system capable of performing a wide range of multi-step molecular biology protocols, including targeted library preparation for next-generation sequencing (NGS). As illustrated in FIG. 2, the DPM chips can be loaded with application-specific reagents during manufacturing, and sealed with a removable adhesive film 200. After film removal 205, end-users can load a sample (e.g., small amounts of blood or purified DNA), and any additional reagents (such as bar-coded adapters), into the chip before placing it into the instrument 210. The instrument can actuate the chip and remain uncontaminated, as all samples, reagents, and waste can be contained within the chip.

Figure 3:
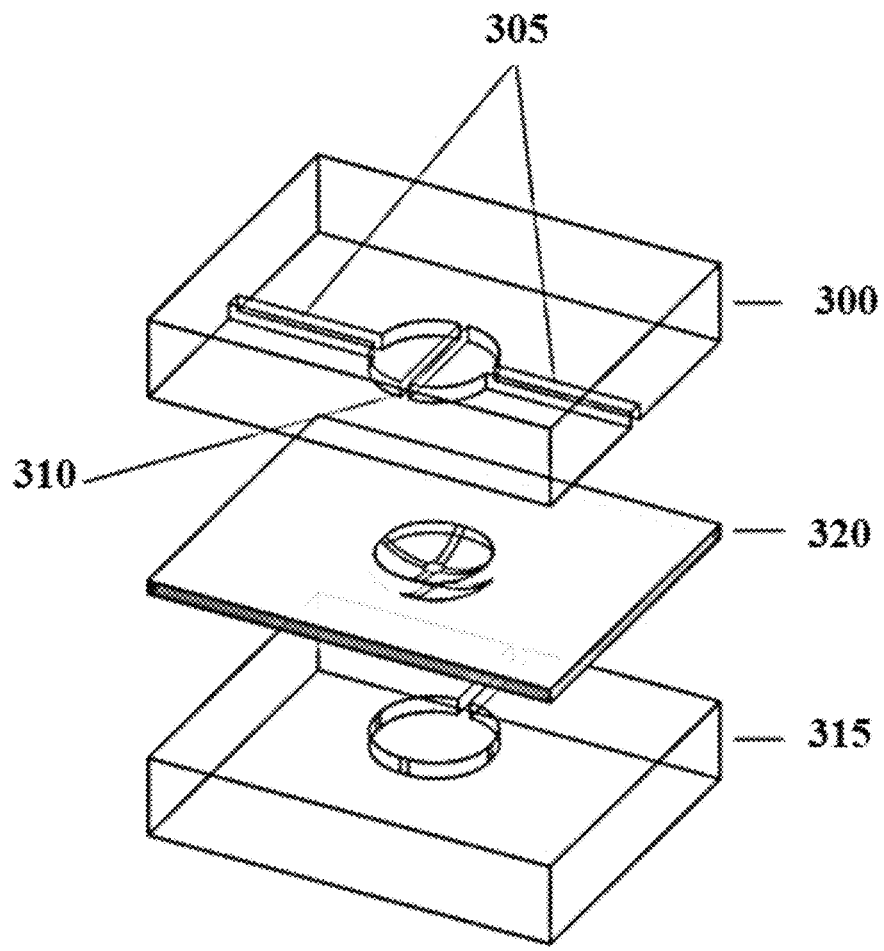
FIG. 3 schematically illustrates a valve of a device of the present disclosure.

The structure of the DPM microfluidic devices of the present disclosure is based on a monolithic membrane valve architecture. As illustrated in FIG. 3, the DPM devices comprise a three-layer structure in which two patterned hard layers surround a central unpatterned elastomeric film. In some embodiments, the patterned hard layer is made from injection molded cyclic olefin polymer (COP). The hard layer is not made from etched glass in some cases. In some instances, the elastomeric film is made from a thermoplastic elastomer (TPE) membrane. In some cases, the film does not include polydimethylsiloxane (PDMS).

FIG. 3 shows a normally closed valve. An actuation layer of the can comprise vias, channels, and chambers for conveying vacuum or positive pressure for film deflection. The actuation layer can be a pneumatic layer to supply (i) positive fluid pressure and/or negative fluid pressure (vacuum), (ii) positive pressure (e.g., upon the application of a mechanical pin), or (iii) the combination of positive pressure and positive or negative fluid pressure. The top fluidic layer can comprise vias, channels, and chambers for reagent/sample reservoirs and fluid flow. Application of vacuum in the pneumatic layer can pull the membrane down away from the valve seat in the fluidic layer (as illustrated) to open the valve, while application of positive pressure can deflect the membrane up against the valve seat, cutting off flow.

FIG. 3 illustrates an example valve of the devices of the present disclosure. The valve can be a diaphragm valve, such as a microscale on-chip valve. The top fluidic layer 300 can carry input and output channels 305 and a valve body comprising two semi-circular sections (e.g., between about 500 and about 1000 um diameter) separated by a valve seat 310 (e.g., between about 50 to about 200 um wide). The bottom pneumatic layer 315 can carry a pneumatic channel connected to a circular chamber of the same diameter as the top semicircular sections. The unpatterned elastomeric film 320 in the center of the three layer sandwich may be deflected either up, by positive pressure applied via the pneumatic channel, or down by vacuum applied via the pneumatic channel. When deflected up, the film can form a tight seal against the valve seat, cutting off flow through the valve. When the film is deflected downward, the valve is open because fluid can flow through the space created between the film and the valve seat. Embodiments of the present disclosure can be combined with features and configurations described in U.S. Pat. No. 8,584,703, which is entirely incorporated herein by reference, to yield yet more embodiments.

It is possible to fabricate either normally open or normally closed valves on the same device. FIG. 3 shows the structure of an example normally closed valve, which includes a valve seat that obstructs flow in the fluidic layer unless the film is actively retracted by vacuum applied to the pneumatic layer. Normally open valves (not shown) omit valve seats, and may include a dome shaped fluidic-side valve body to enhance film sealing and minimize dead volume in the closed (pressurized) state.

Figure 4:
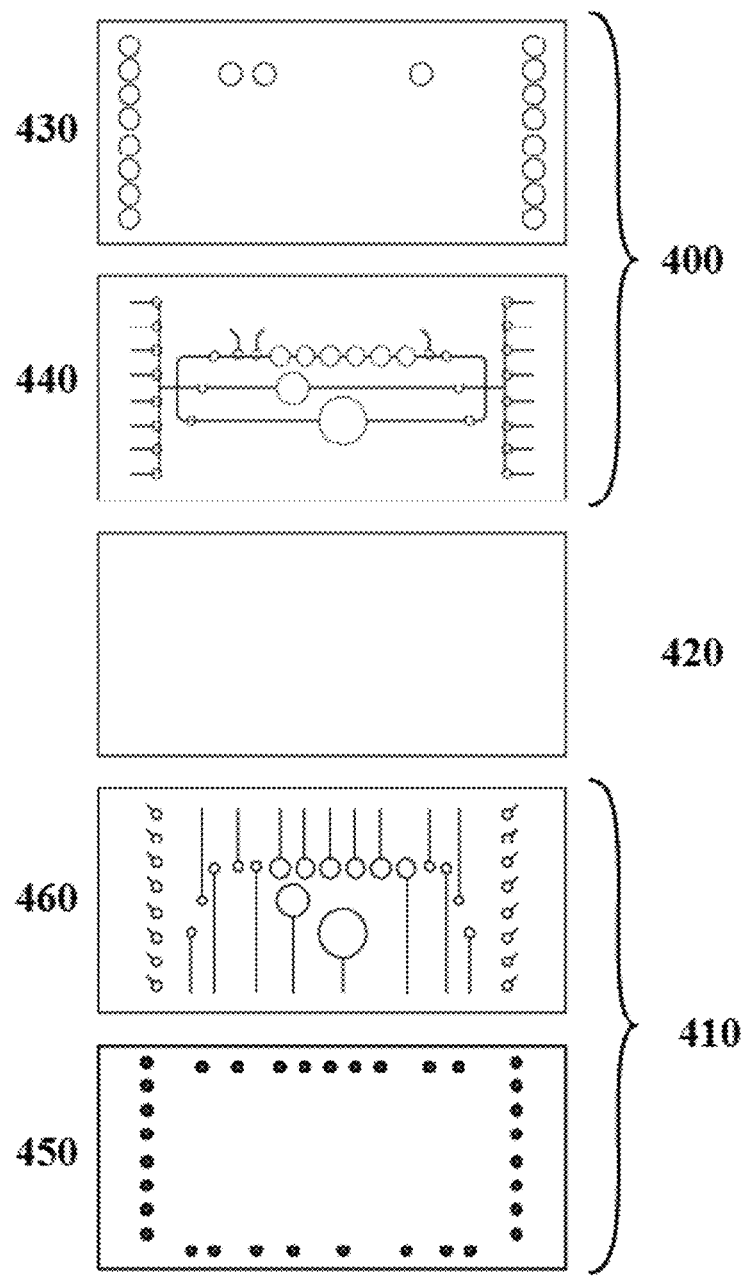
FIG. 4 schematically illustrates separate layers of the device of the disclosure.

FIG. 4 illustrates an example method for manufacturing the device of FIG. 1. Layer 1 400 (fluidics) and Layer 3 410 (pneumatics) can comprise a hard thermoplastic (typically COP) patterned on one side and with through holes serving as input/output ports or wells. Layer 2 420 can include an unpatterned elastomeric film sandwiched in between Layers 1 and 3. Layers 1 and 3 can be fabricated by injection molding or alternatively by hot embossing followed by hole drilling by CNC machining Layer 1 can have two sub-layers and/or have different openings on each side of a single layer, shown here as top wells 430 and fluidics 440. Similarly, Layer 3 can have two sub-layers and/or have different openings on each side of a single layer, shown here as bottom wells 450 and pneumatics top 460. Adhesion of the elastomeric film to hard thermoplastic surfaces may be accomplished by a number of methods, depending on the composition of the film. In some embodiments, the film can comprises a styrene-ethylene-butylene-styrene (SEBS) or other thermoplastic elastomer, surfaces can be activated by oxygen plasma treatment, and the sandwich can be assembled by lamination at moderate temperatures (e.g., about 100° C.).

Figure 5:
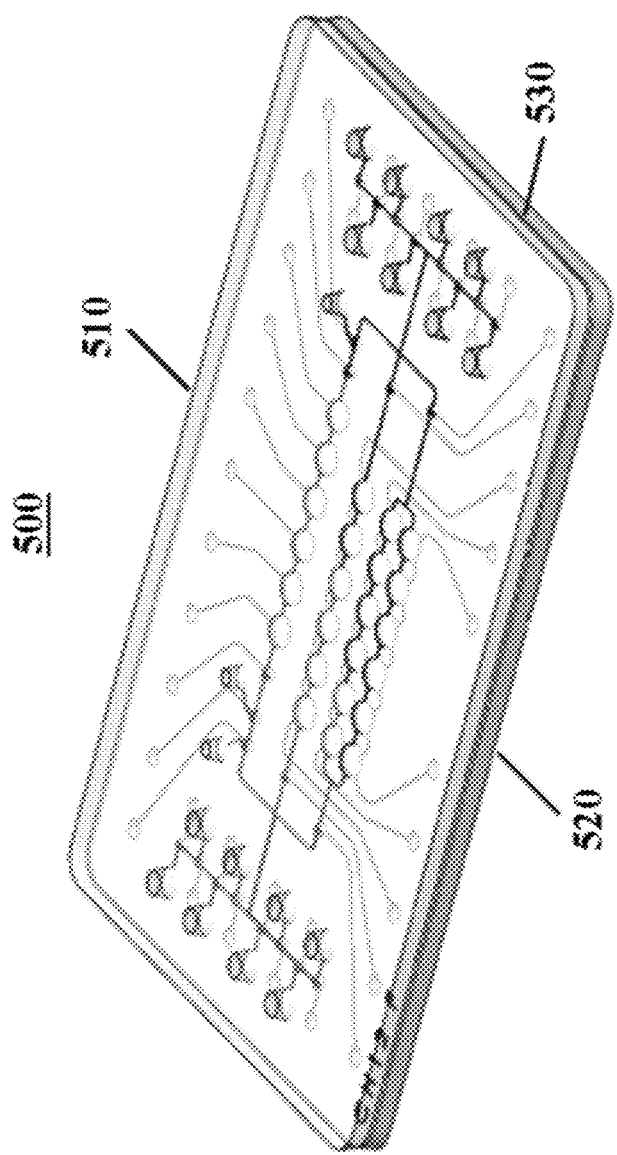
FIG. 5 schematically illustrates the layers of the device of the disclosure.

A schematic drawing of the assembled, example chip 500 is shown in FIG. 5. The chip 500 has a fluidic layer 510, a pneumatic layer 520 and a TPE film 530 there between. FIG. 5 is a three-dimensional CAD model of an example DPM processor chip that can be used to create a CNC-machined aluminum mold for injection molding the chip's fluidic and pneumatic layers. In this example, feature depths and channel widths are both 100 μm (in both layers), and valve and pump diameters are 750 μm and 2 mm, respectively. Valve seat widths for normally closed valves are 150 μm. Layer thicknesses are both 1.2 mm, and overall chip lateral dimensions are 60 mm×38 mm.

The characteristics of the elastomeric film, which can also function as the bottom surface or floor of the fluidic channels, valves, and pumps, can be important to the performance of the device. The film can be chemically compatible with the reagents, enzymes, and nucleic acids processed in the chip and stable to temperatures of up to 100° C. (e.g., for thermocycling), while remaining nearly impermeable to the pressurized air used to actuate the pumps and valves. Accordingly, in some cases, DPM chips provided herein include TPE films. TPEs are polymeric materials that combine the elasticity of rubber with the thermoforming capabilities of thermoplastics. In contrast with thermoset polymers such as PDMS, TPEs can be extruded, injection molded and hot embossed, all of which can aid in low-cost mass production. In addition, TPE materials can be less expensive than other materials used in microfluidics. TPEs can be block copolymers in which "hard" and "rubbery" polymers segregate into distinct but connected microscopic domains. Softening of the hard component at high temperatures can permit thermoforming. Varieties of TPE compositions with a wide variety of mechanical and chemical characteristics are available. Non-limiting examples of TPEs include thermoplastic polyurethanes, styrenic thermoplastic elastomers, anionic triblock copolymers, polyolefin-based thermoplastic elastomers, halogen-containing polyolefin-based thermoplastic elastomers, dynamically vulcanized elastomer thermoplastic blends, polyether ester elastomers, polyamide-based thermoplastic elastomers, ionomeric thermoplastic elastomers and polyacrylate-based thermoplastic elastomers. Additional examples of TPEs are described in Thermoplastic Elastomers, $3^{rd}$ Edition, Eds: G. Holden, H. R. Kricheldorf, R. P. Quirk, Hanser, 2004, which is entirely incorporated herein by reference.

TPE compositions can provide key advantages for microfluidics, with such advantages that include decreased gas permeability and facile bonding. TPE films can provide decreased air and small molecule permeability compared with PDMS films of similar thickness and mechanical modulus. This property allows air pressure to be used for actuation of membrane pumps and valves, as permeation of air into the fluid layer is negligible. The use of air pressure can significantly reduce end-user set-up effort (user burden) as well as instrumentation cost and complexity. The reduced small molecule permeability (and low extractables) characteristics of TPE films can also increase their chemical compatibility in molecular biology applications.

The inherent adhesive-like properties of TPEs can simplify assembly of the three-layer chip structure. This is because TPE films can strongly adhere, and effectively bond to, low surface energy thermoplastic surfaces with the application of only moderate pressure and temperature. In some cases, stable three layer chips are able to withstand greater than 30 psi pneumatic pressures at thermocycling temperatures (e.g., 100° C.) and can be assembled simply by passing the device sandwich through an inexpensive commercial laminator. In addition, the surface and bonding properties of thermoplastic and TPE layers can be readily modified by UV-ozone (UVO) treatment.

Dual Actuation and Pin Valves

Figure 6:
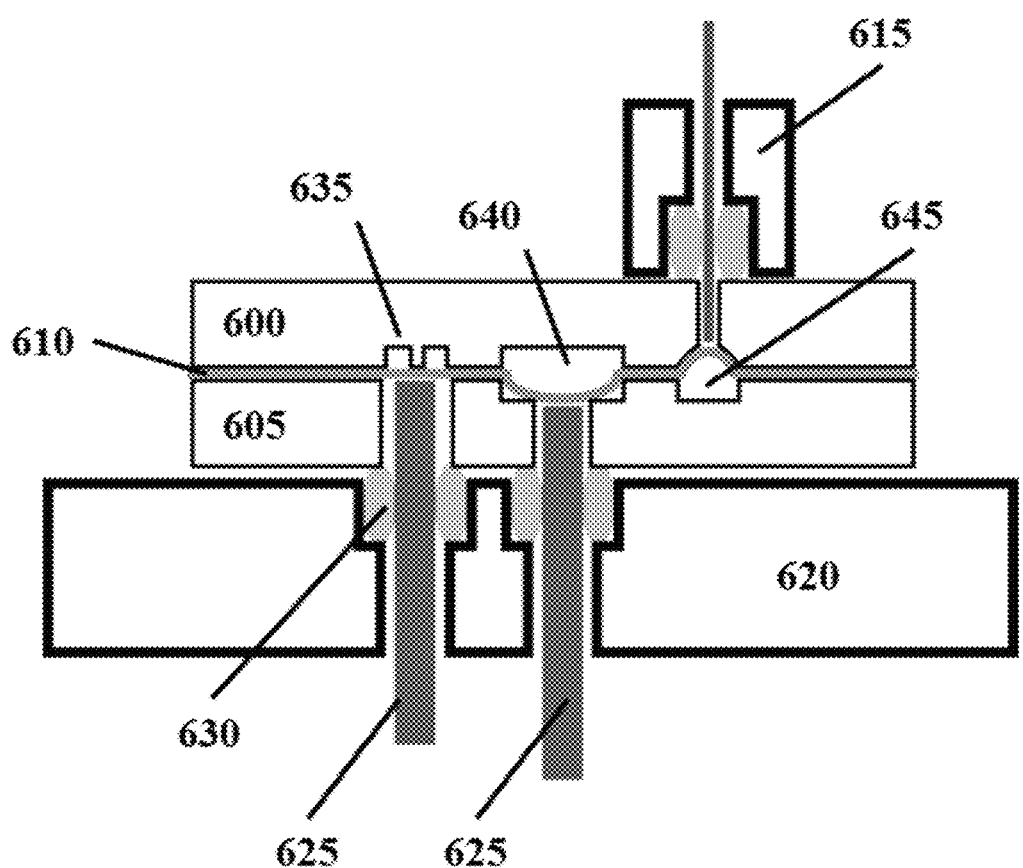
FIG. 6 schematically illustrates dual actuated valves of the present disclosure.

The present disclosure also provides devices with dual-action and/or pin valves. The dual action valve can augment pneumatic actuation with mechanical actuation (e.g., pushing on the film with pins). Pneumatic actuation can be with the aid of positive pressure (e.g., pressurized gas, such as air) or negative pressure (e.g., a vacuum). Pneumatic actuation and mechanical actuation (e.g., with a pin) can be simultaneous, or can occur in an alternating and sequential manner (e.g., pneumatic actuation followed by mechanical actuation, or vice versa). In some situations, the dual action valve does not replace pneumatic actuation. Referring to FIG. 6 depicting example pin valves, the fluidic layer 600 and pneumatic layer 605 can have a flexible membrane 610 disposed there between. Manifolds can be displaced adjacent to the fluidic layer 615 and/or the pneumatic layer 620, through which pins 625 or other mechanical members can be actuated. The manifolds can have o-rings 630 that can preserve pneumatic pressure (e.g., vacuum), and the pins can slide through the o-rings. Fluidic and pneumatic channels are not shown in FIG. 6.

For example, a normally closed valve 635 has a pin 625 that slides through an o-ring 630. The pin can exert additional pressure on the film to seal the film against the valve seat. This valve configuration can be useful for sealing valves during thermocycling for example.

A pump 640 (having no valve seat) can also be augmented with a mechanical pin. Here, the pin can release the film from any undesired attachment to the bottom of the pneumatic chamber. This use of a pin can also be useful for preventing film adherence associated with thermocycling, as the film can adhere to the chamber bottom after exposure to temperatures in excess of approximately 75° C. When such adherence occurs, the pump is effectively inactivated (malfunctions) because the film can no longer be deflected up by pneumatic pressure.

A normally open 645 (dome) valve can also be augmented with a mechanical pin. Here, the pin can release the film from top of the fluidic (dome) chamber. This implementation can take advantage of the attachment of the TPE film and allow storage of liquid reagents in the chip. This strategy can allow the valve (e.g., connected to the storage reservoir) to remain closed before chip use (e.g., for several months). Stable closing can be achieved during manufacturing by application of pneumatic pressure at a suitable temperature (e.g., 90° C.). The valve can then remain closed until the film is mechanically deflected by the pin.

Figure 7:
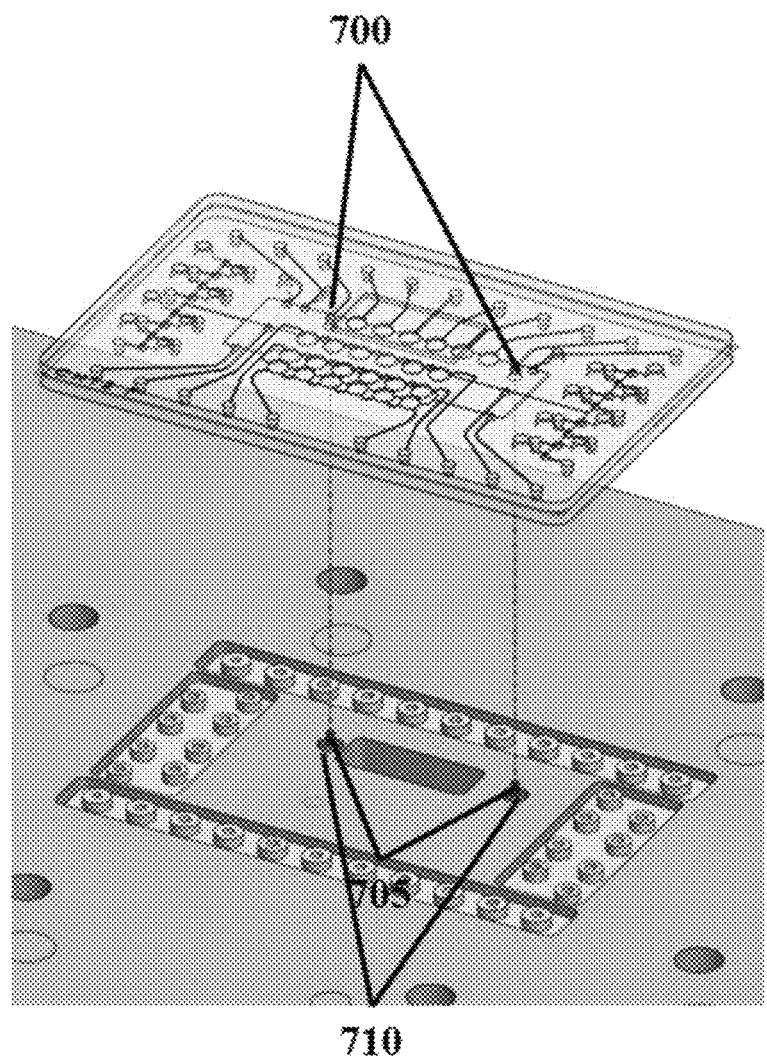
FIG. 7 shows a top view of dual-actuation valves for thermocycling.

FIG. 7 shows a top view of example dual-actuation valves for thermocycling. In some cases, pneumatically actuated valves may provide insufficient sealing capacity during thermocycling. Much higher closing forces can be applied to valve membranes mechanically. The two indicated valves 700 are actuated by pressure and/or vacuum and mechanical force, the mechanical force transmitted by movable pins 705. The pins can be actuated by small pneumatic cylinders that can supply a large and precise force to valve membranes. The pins can access the membrane through pneumatic-side holes. Pressure and/or vacuum can be preserved by o-rings gaskets 710 that contact the bottom of the chip and provide air-tight seals around the pins.

Figure 8:
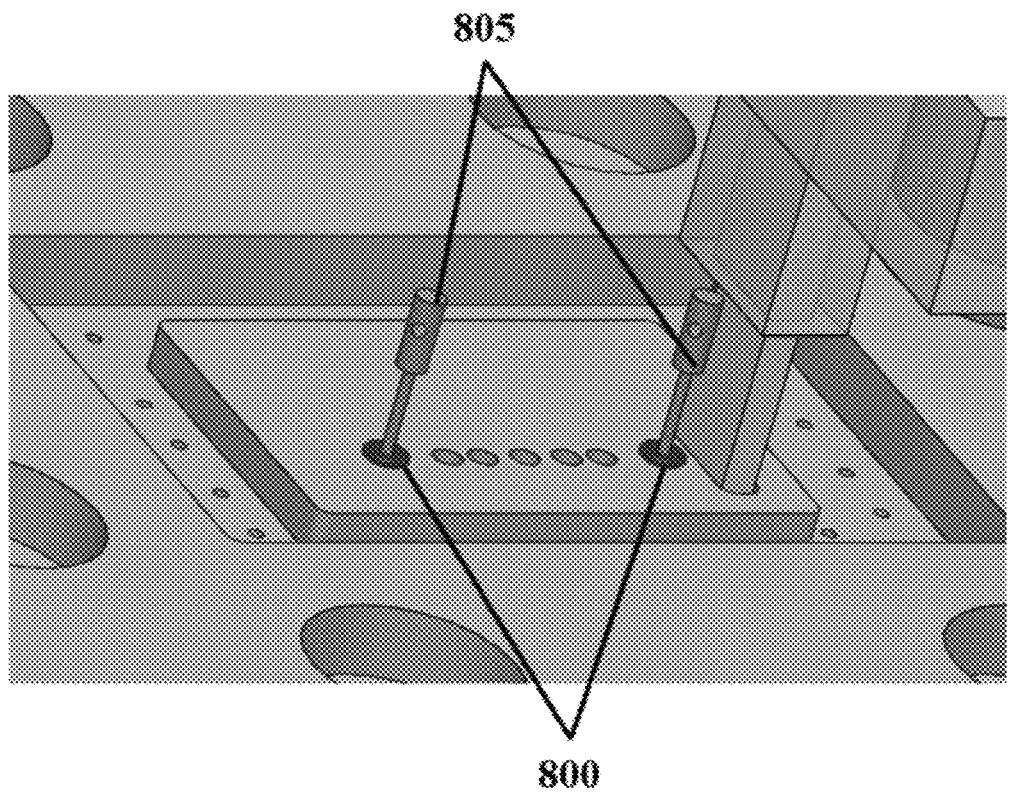
FIG. 8 shows the backside view of the valves of FIG. 7.

FIG. 8 shows the backside view of the valves of FIG. 7. Additional gaskets 800 on the backside of the manifold can provide air-tight seals to the pins 805. Pins can slide through gaskets to actuate valves in the chip. Silicone vacuum grease may be used to reduce friction.

Figure 9:
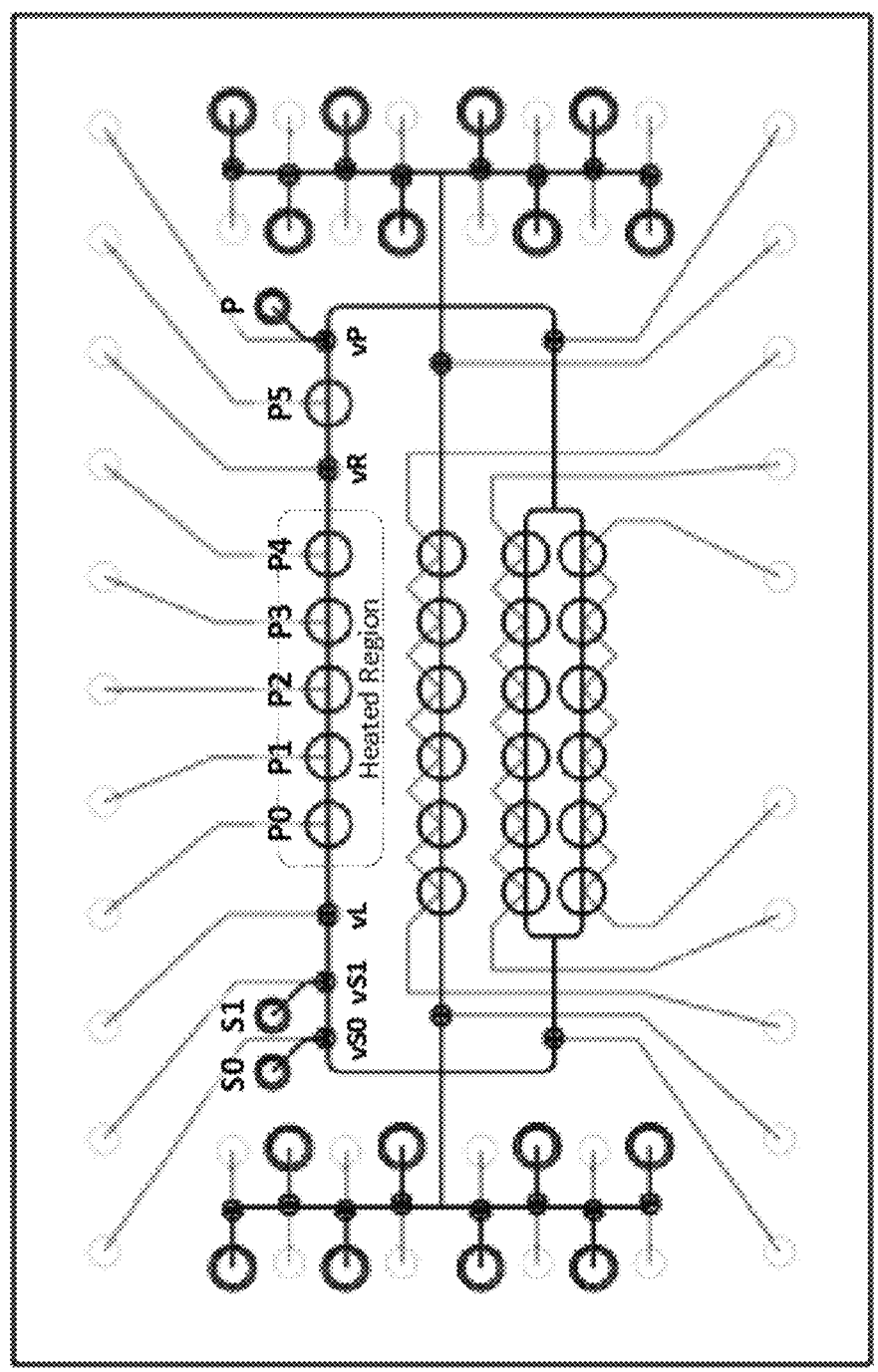
FIG. 9 shows a chip that has been design to accommodate dual-actuated valves.

FIG. 9 shows a chip that has been design to accommodate dual-actuated valves. The main processor has (i) vS0 and vS1 valves out of the chip's pressurized section, (ii) accommodated mechanical actuation at valves vL and vR, and (iii) isolated thermocycling pumps P0-P4.

DPM Chip Architecture and Operation

Figure 10A:
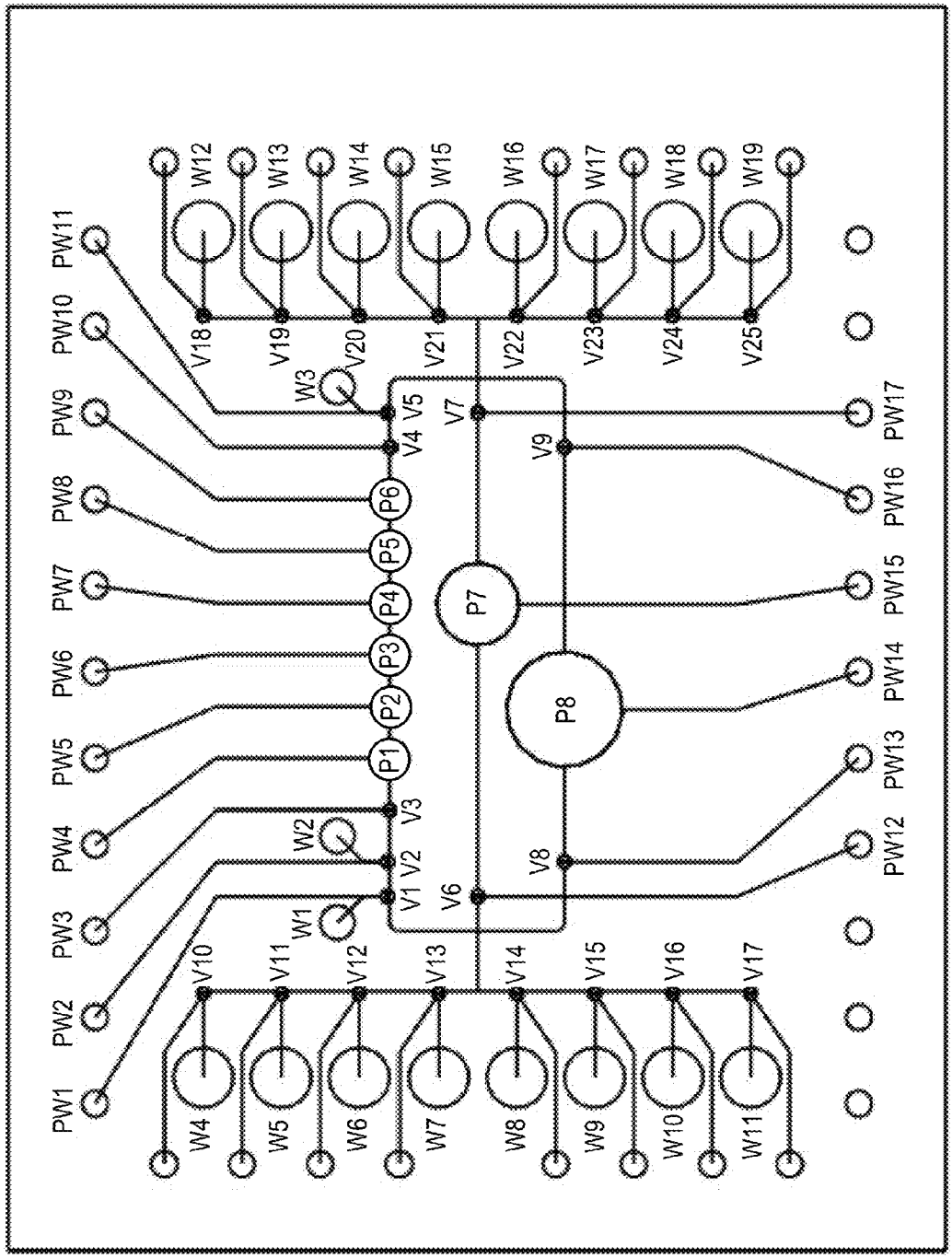
FIG. 10A schematically illustrates a microfluidic device of the present disclosure.
Figure 10B:
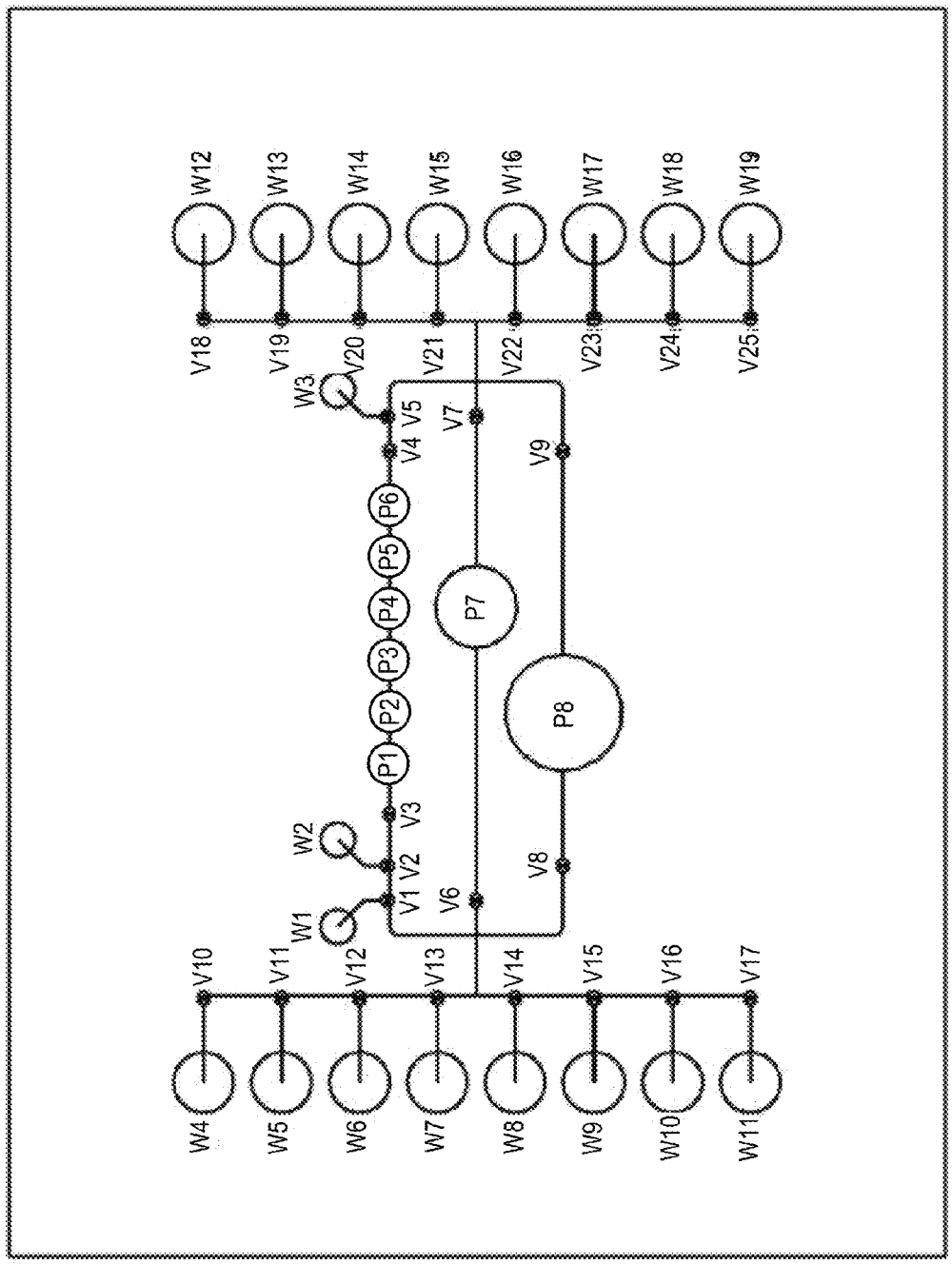
FIG. 10B shows fluidic (first face) patterns, as well as through-hole positions.
Figure 10C:
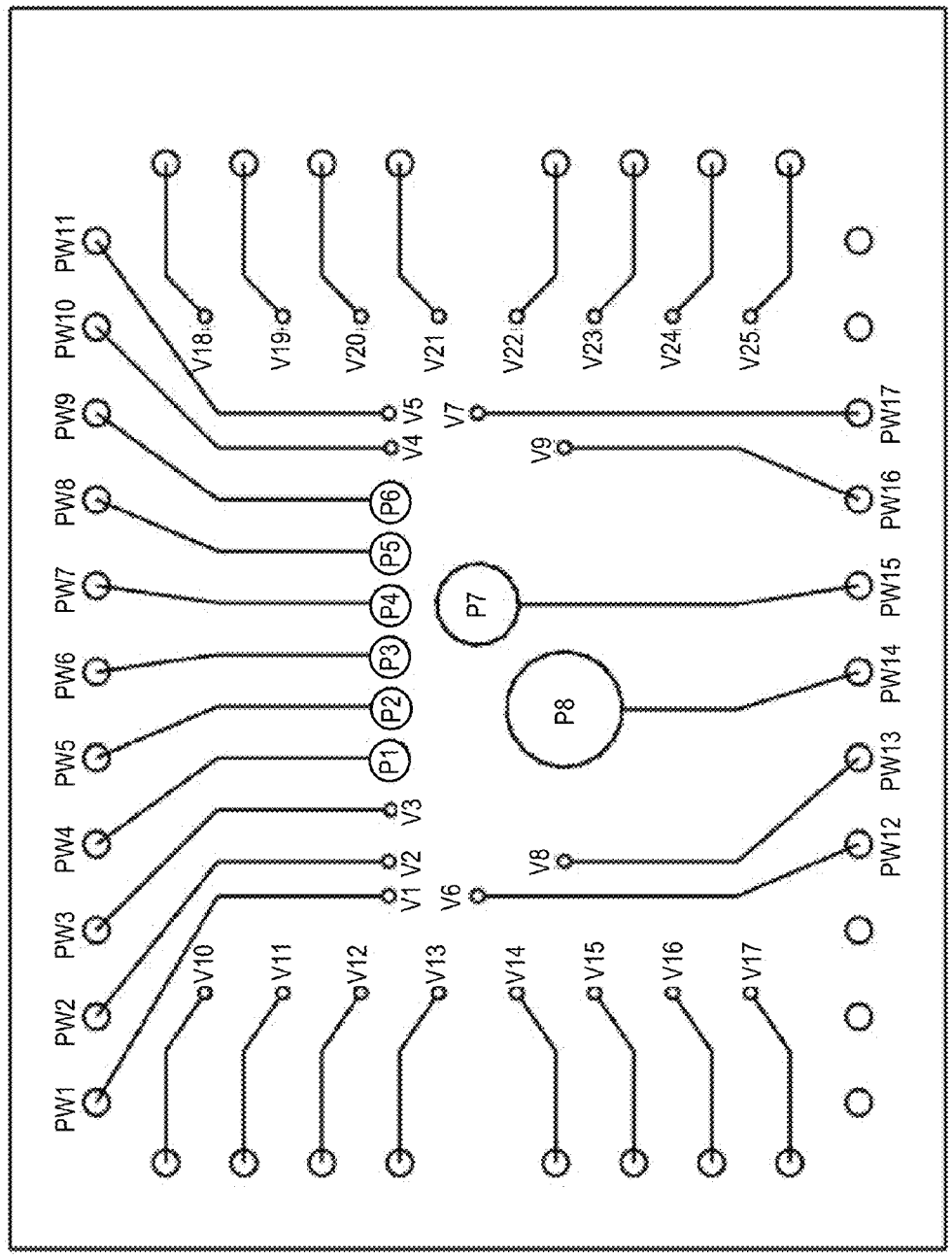
FIG. 10C shows pneumatic (first face) patterns, as well as through-hole positions.

The present disclosure illustrates the principles of the invention by way of description of two chip architectures, along with examples of operation of the chips. These are but two detailed embodiments, and do not limit the scope of the invention. In a first example of a DPM chip of the present disclosure, FIG. 10A shows a composite schematic diagram of an example microfluidic device, which comprises three layers: fluidics layer, elastic layer (film), and pneumatic layer. The fluidic and pneumatic layers can be made from a hard thermoplastic such as cyclo-olefin polymer (COP). The film layer can be made from an elastomer layer that is, for example, between about 50 micrometers ($\mu$m) and about 500 $\mu$m thick. The film layer can be sandwiched between the two hard layers, which are, for example, about 0.5 to about 5 millimeters (mm) thick. The fluidic and/or pneumatic layers can be fabricated from other hard materials including glass, fused silica, and silicon, or the device may be fabricated entirely from elastomeric materials. The device can have more than three layers (e.g., 4, 5, 6, 7, 8, 9 or 10 layers or more). The fluidic and pneumatic layers can both have first patterned surfaces comprising channels, valve or pump chambers, as well as second unpatterned surfaces. In some cases, both first and second surfaces are patterned. Feature depths can be between about 10 and 500 $\mu$m, and channels can be between about 10 and about 500 $\mu$m wide. In addition, the fluidic and pneumatic layers can carry through-holes connecting channels on the first faces to the second faces. FIG. 10B and FIG. 10C show examples of fluidic and pneumatic (first face) patterns, as well as the through-hole positions. The device can be assembled with the fluidic and pneumatic patterned first surfaces facing the film.

Fluidic and pneumatic connections to the chip can be made via the through-hole termini on the second (outward facing) fluidic and pneumatic layer faces, respectively. The fluidics layer through-holes can function as fluid-containing wells or reservoirs and provide input and/or output ports for the device. They may be unpressurized or pressurized by application of a pneumatic manifold (not shown). Pressurization may be useful for performing polymerase chain reaction (PCR) or other type of nucleic acid amplification reaction. The pneumatic layer through-holes can function as pneumatic ports connecting the device's pumps and valves to external pressure and vacuum sources (not shown).

Referring to FIGS. 10A-10C, the central section of the device, comprising pumps P1-P8, valves V1-V9, and wells W1-W3, function as a general purpose fluid processor capable of mixing up to six reaction components, incubating reactions at elevated temperature, thermocycling reactions, and purifying nucleic acids (DNA and RNA) using magnetic particles (e.g., beads). The central processor can be fluidically connected to two input/output systems that supply reaction components, reagents, bead and wash solutions, etc., as well as provide access to waste reservoirs. These two systems, referred to as reagent rails, or simply rails, collectively comprise valves V10-V25 and wells W4-W19.

Figure 11:
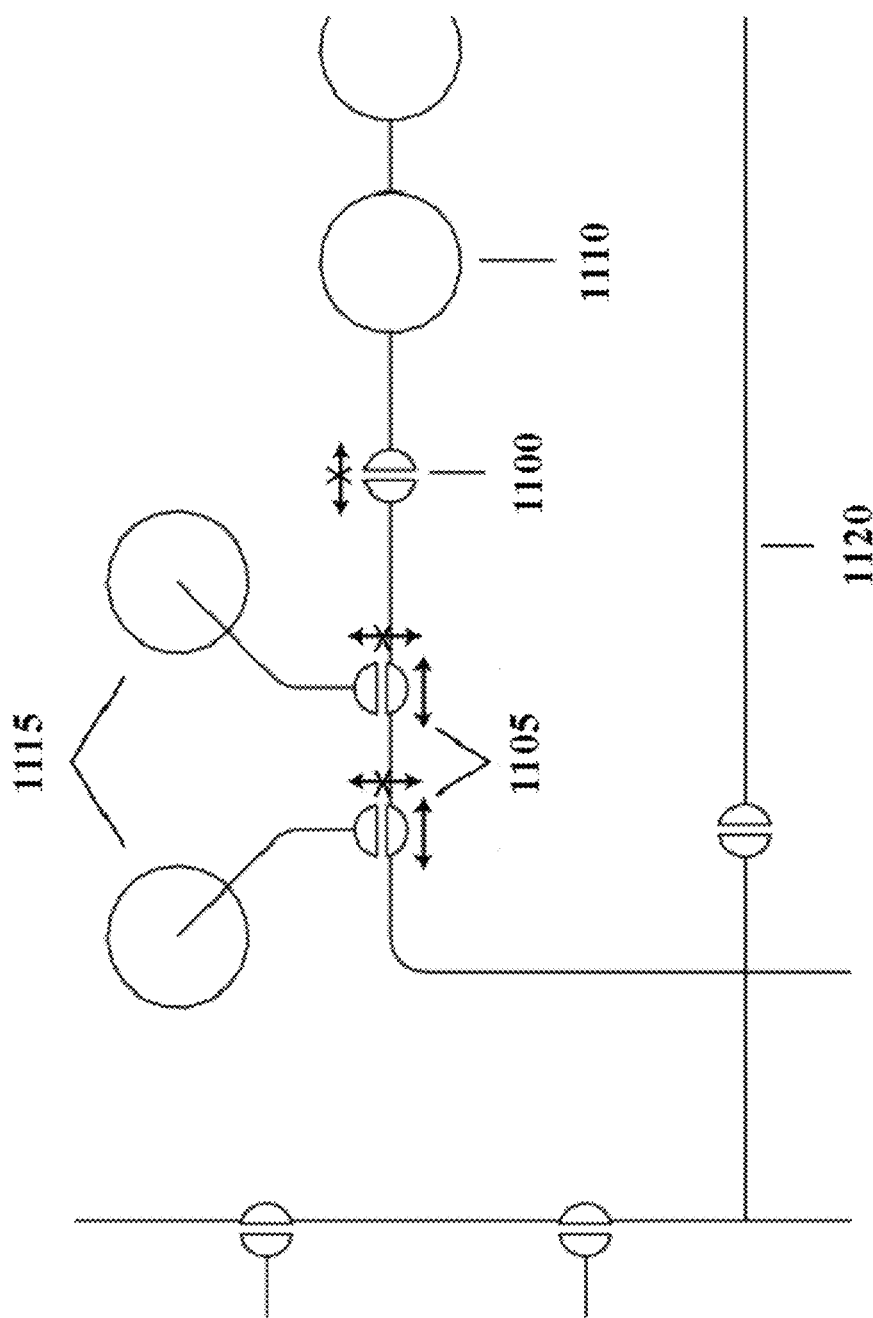
FIG. 11 schematically illustrates valving and pumping schemes of a microfluidic device of the present disclosure.

FIG. 11 illustrates example valving and pumping schemes of a microfluidic device. Flow is controlled by valves 1100, which valves permit or cut-off flow as described above. In addition, FIG. 11 illustrates the device having valve structures called flow-through valves 1105. Flow-through valves remain open in the direction indicated by the arrows without X's. In this configuration, the valve seat only regulates flow in the perpendicular direction (to or from the wells), as indicated. FIG. 11 also illustrates device pumps 1110, which are can be large valves lacking valve seats. Wells 1115 and channels 1120 are also shown.

With reference to FIGS. 10A-C, pumps P1-P8 are responsible for the pumping and mixing functions in the device. In this example design, pumps P1-P6 have identical structures and hold identical fluid volumes when their respective films are pulled down by vacuum applied via their respective pneumatic control lines. When positive pressure is applied, a pump can expel its fluid volume into the fluidically connected adjacent channels. In this emptied state, pumps can provide a flow cut-off function, similar to the valves (with valve seats) described herein.

In one example, the device of FIG. 10A-C can be used to digitally mix two volumes. Assuming that the initial (and default) state of the device has all pumps and valves closed. Referring to FIG. 10B, up to five identical small, discrete (digital) volumes may be mixed by pumps P1-P6 as follows. A first discrete volume (V) can be drawn into P1 from, for example, W7 by opening valves V3 and V13 and then P1. The volume in P1 may then be transferred to P2 by closing V3 and then simultaneously closing P1 and opening P2. Next, a second discrete volume (V) may be drawn into P1 from W1 by opening V1 and V3 and then P1. At this point, the two discrete volumes are in adjacent valves (P1 and P2) may be mixed by first closing V1 and V3, and then simultaneously closing P1 and opening P3. This action can force the contents of P1 to flow through P2, creating convection in P2. The result is that the two volumes, now residing in P2 and P3, are substantially well mixed (e.g., having a maximum concentration gradient of no more than 10%, 5%, 3%, 1%, 0.5% or 0.1%). This process may be repeated for one or more cycles to further mix the two volumes, simply by propagating the pattern to the right, through the remaining valves (up to and including P6), and back to the left, up to and including P1.

In another example, the device of FIG. 10A-C can be used to digitally mix 3-5 volumes. Three to five discrete volumes may be similarly mixed with simple modifications to the above described process. For example, three, four, or five discrete volumes may first be loaded into P1-P3, P1-P4, or P1-P5, respectively. In all of these cases, at least one pump will remain empty, permitting a similar mixing pattern to be used. In the three volume case, for example, P4, P5, and P6 remain empty, and the three volumes (initially in P1-P3) may be mixed by (a) closing P1 and opening P4, (b) closing P2 and opening P5, (c) closing P3 and opening P6. The pattern may then be reversed to continue mixing in the opposite direction.

In another example, the device of FIG. 10A-C can be used to digitally mix six volumes. In this case, P1-P6 are all initially filled and mixing utilizes P7, which is designed to have an internal volume equal to the sum of P1-P6 (6V). Transfer of the six volumes in P1-P6 to P7 can be accomplished by opening V6-V9, and then (nearly) simultaneously closing P1-P6 and opening P7. Transfer of the 6V volume in P7 back to P1-P6 can be accomplished by (nearly) simultaneously opening P1-P6 and closing P7.

The device of FIG. 10A-C can be used to purify magnetic beads, which can comprise the operations of mixing, washing, drying, and elution, where elution can comprise the operations of resuspension, recapture, separation, bead elimination and transfer.

Magnetic bead based purification of nucleic acids can be accomplished by mixing an equal volume of magnetic beads (e.g., carboxylated polymer paramagnetic beads) in a slurry containing salt and either low molecular weight polyethylene glycol (PEG) or alcohol (ethanol or isopropanol). In the example device described above with respect to FIGS. 10A-C, one, two, three, or six volumes of nucleic acid containing solution(s) can be mixed with equal volumes of bead solution using simple modifications of the procedures described above. For example, one or two volumes can be handled entirely within P1-P6 by mixing them with one or two volumes of bead solution, respectively. This is because four or two pumps remain initially empty, respectively, allowing the mixing protocols outlined above to be employed. In another example, nucleic acid mixtures of three volumes may be mixed with the aid of P7 by first completely filling P1-P6 with three additional volumes of bead solution, followed by mixing between P1-P6 and P7, as described above. In another example, nucleic acid mixtures of six volumes may be mixed with the aid of P7 and P8, first by filling P7 with bead solution (equal in volume to the nucleic acid solution occupying P1-P6), and mixing between (P1-P6) along with P7 and P8 by transferring P1-P6 (6V) and P7 (6V) into P8 (12V), and back again. These transfers can be accomplished using valves V3, V4 and V6-V9.

Figure 12:
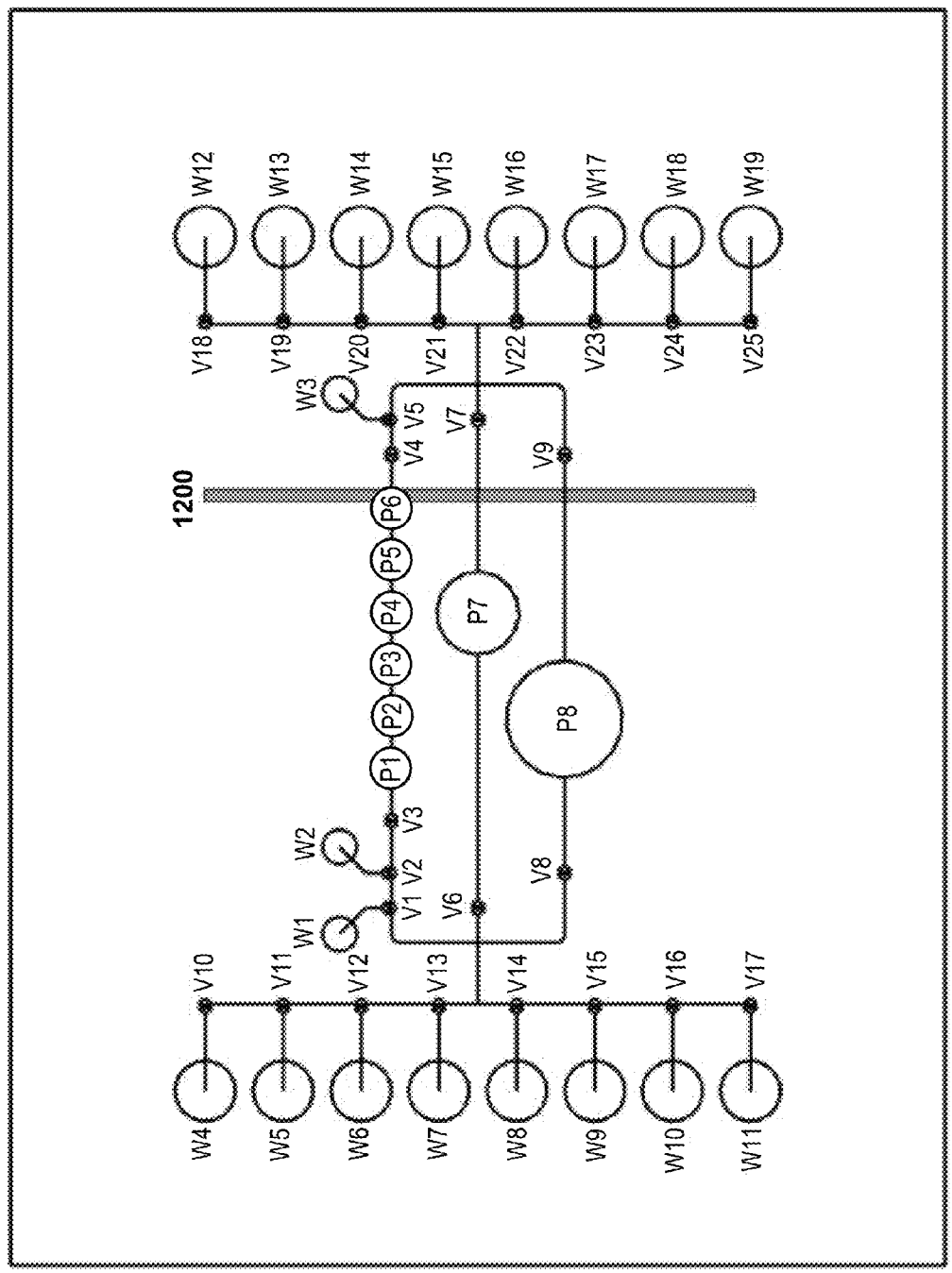
FIG. 12 schematically illustrates capturing paramagnetic beads with the aid of an external magnet.

After mixing is completed, magnetic beads may be washed and dried. The magnetic beads can be captured in P6 with the aid of an external magnet, as illustrated in FIG. 12. Magnetic capture can be accomplished by pumping mixed magnetic bead solutions (initially residing in P1-P6, P7, or P8) through P1-P6, across the magnet 1200, to a designated waste well in the right rail (wells W12-19). Once beads are concentrated in P6, bead wash solution (e.g., 70% EtOH) may be pumped from one of rails into, for example P7, transferred to P1-P6, and then pumped to the right side waste well by P1-P5. Similarly, beads may be dried by pumping air, sourced from another rail well, in the same manner.

Following washing and/or drying, the bound nucleic acids can be eluted from the beads. Elution can involve the following series of steps: (a) resuspension, (b) recapture, (c) separation, (d) bead elimination and (e) transfer.

For resuspension, with the magnet removed, the dried beads in P6 can be mixed with one volume of elution buffer (e.g., Tris-EDTA (TE) buffer) to release nucleic acids from the beads, for example, pumped from P5 into P6. Where appropriate, additional resuspension may be achieved via additional reciprocal transfers between P5 and P6.

For recapture, beads in P6 can be recaptured by repositioning the magnet adjacent to P6.

For separation, eluate solution in P6 containing released nucleic acids is transferred to P5, leaving the beads behind in P6. Elution is now complete.

For bead elimination, the beads remaining in P6 may be washed out of P6 by first removing the magnet and then pumping bead elimination solution (e.g., TE or dilute NaOH) into P6 and then to waste.

For transfer, the eluate in P5 may be transferred to a product output well, such as for example, well W3. Alternatively, it may remain within one of the processor pumps (P1-P6) so that it can be mixed with additional reagents for further processing.

Figure 13:
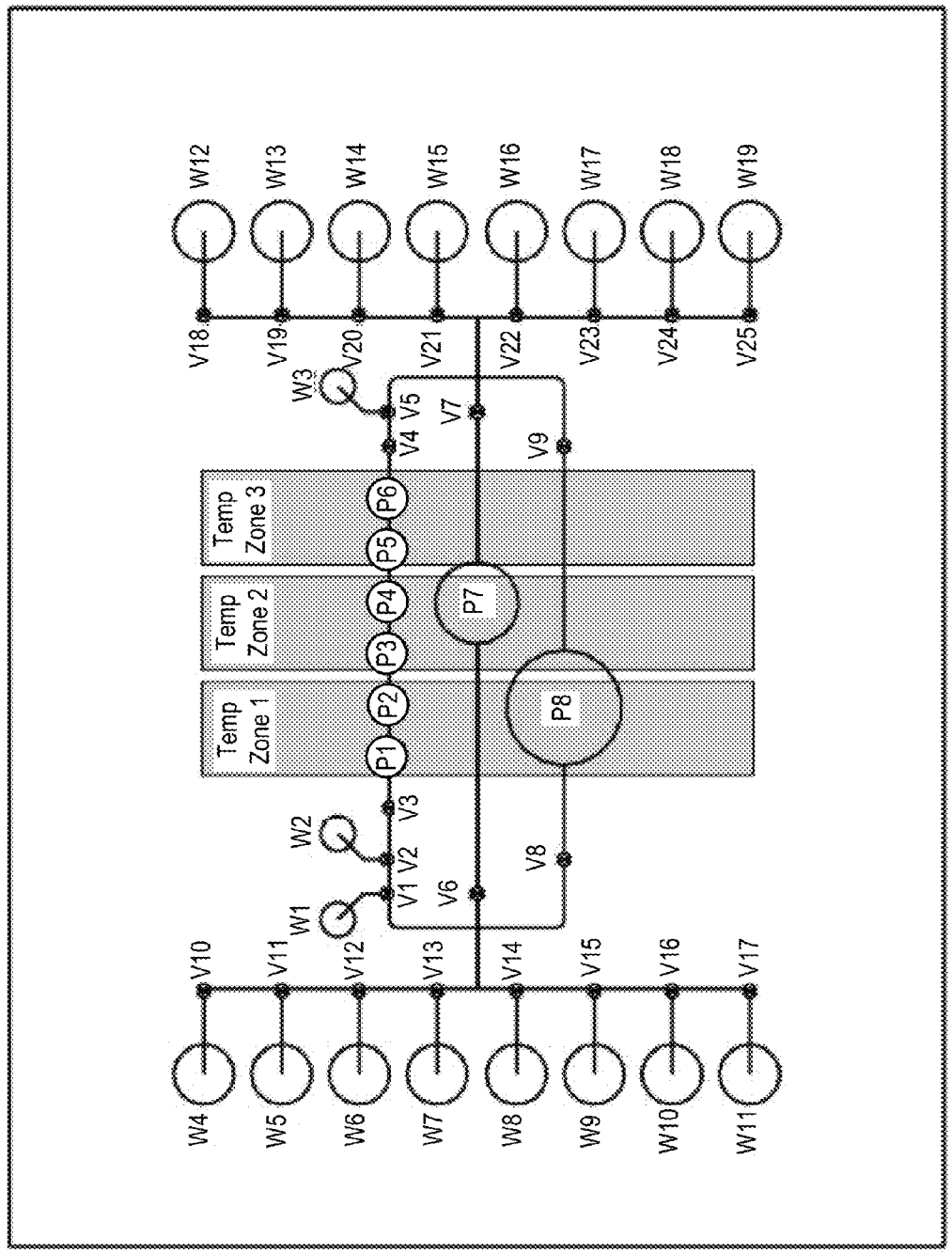
FIG. 13 schematically illustrates incubating one to six volumes at a controlled temperature.

The device of FIG. 10A-C can be used for temperature controlled incubation. Pumps P1-P6 may incubate one to six volumes at a controlled temperature. As illustrated in FIG. 13, this can be accomplished by heating and/or cooling (e.g., resistive heaters or thermoelectric Peltier heat pumps) top and/or bottom surfaces of chips. Division into two or more heat control zones provides added flexibility for nucleic acid amplification, such as PCR (described below).

The device of FIG. 10A-C can be used for nucleic acid amplification, such as PCR. Referring to FIG. 13, reactions occupying one or two pump volumes can be rapidly thermocycled between two temperatures for multiple-step nucleic acid amplification (e.g., two-step PCR) by holding, for example, temperature zone one ("Temp Zone 1") at an annealing temperature (e.g., approximately 65° C.); holding temperature zone three ("Temp Zone 3") at a denaturation temperature (e.g., approximately 95° C.); and transferring the reaction between P1 or P2 (or both) and P5 and P6 (or both). In this case, temperature zone two ("Temp Zone 2") can serve as a thermal isolation region between the temperature zone one and temperature zone three. Alternatively, the three temperature zones may be used for three-step nucleic acid amplification (e.g., three-step PCR) by holding temperature zone two at an intermediate extension temperature (e.g., approximately 72° C.), and appropriately positioning the reaction among pumps P1-P6. Alternatively, the three temperature zones may be maintained at identical temperatures and all three cycled together between annealing and denaturation (or annealing, extension, and denaturation) temperatures. In this case, reactions may either remain stationary or cycle among pumps P1-P6.

Figure 14:
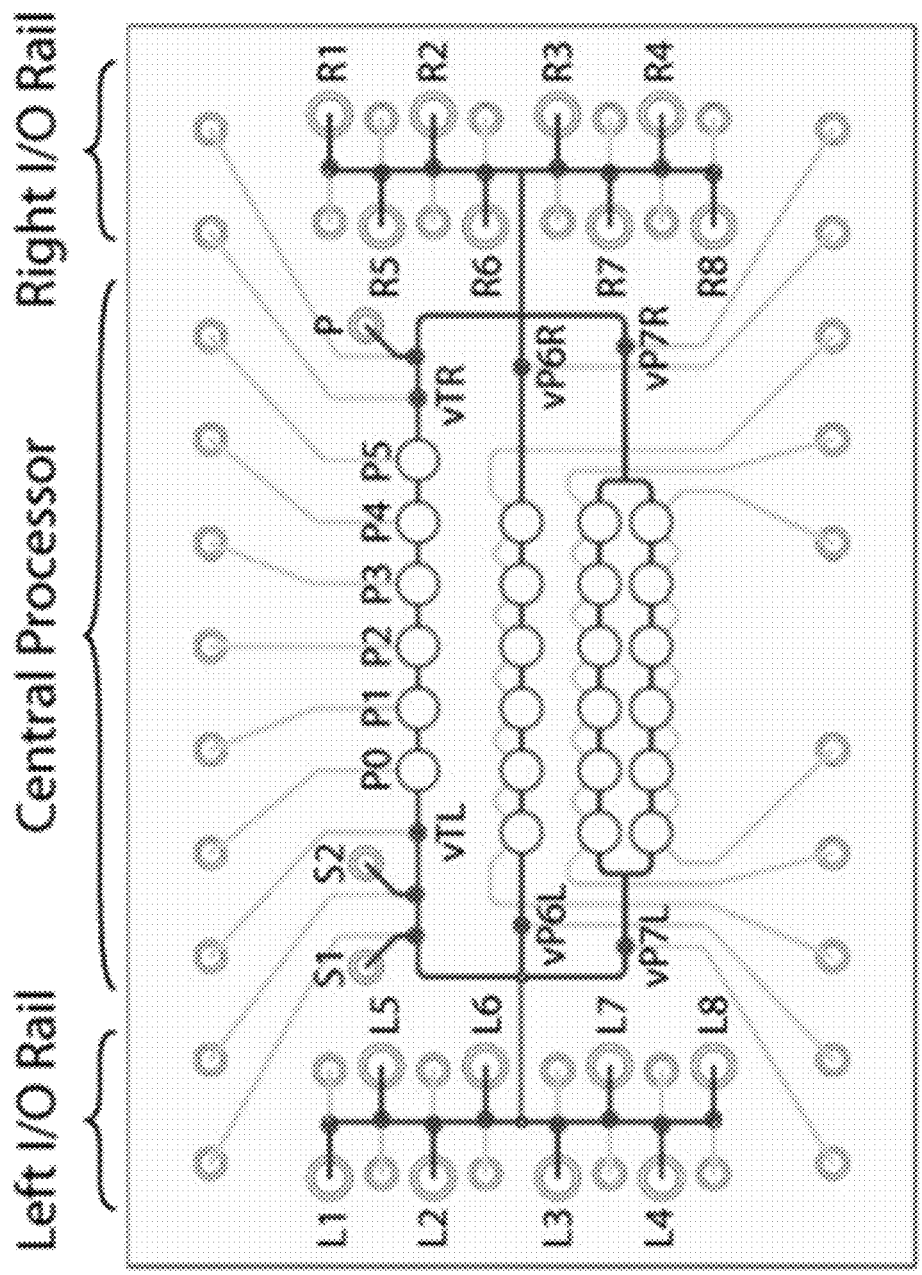
FIG. 14 schematically illustrates an example of a DPM chip where the fluidic layer features are depicted with black lines, the pneumatic layer features with gray lines, and vias with double circles.

Molecular biology protocols can be multi-step procedures comprising one or more of (i) mixing and/or incubation, (ii) purification, and (iii) thermocycling operations. FIG. 14 schematically illustrates an example general-purpose DPM chip architecture capable of providing these functions, with the central processor region of the DPM chip shown in FIG. 15. The device comprises three modular subsections: Left I/O Rail, Central Processor, and Right I/O Rail. Left and Right I/O Rails each comprise eight fluid input/output ports (reservoirs L1-L8 and R1-R8, respectively) with their associated normally closed control valves (unlabeled). Together, the left and right rails provide the Central Processor with access to sixteen fluidic ports for reagent input and/or waste output. The Central Processor can comprise one or more sub-branches, the example device shown in FIG. 14 and FIG. 15 having three sub-branches: (i) a main processor branch comprising six identical normally open "single volume" pumps (P0-P5) and three I/O ports; two for sample input (reservoirs S1, S2) and one for product output (reservoir P) and their associated normally closed control valves (unlabeled), (ii) a P6 Pump Array branch comprising an array of six normally open pumps, and (iii) a P7 Pump Array branch comprising an array of twelve normally open pumps. Each of the three branches is gated on left and right sides by normally closed valves (vTL, vTR, vP6L, vP6R, vP7L, vP7R) allowing each branch to be selectively connected to another branch, Left or Right I/O Rails, or isolated. Note that unlike P0-P5, which are individually actuatable, pumps in pump arrays P6 and P7 operate in parallel, as their pneumatic control lines are linked. Pump array P6 can be designed to hold the contents of P0-P5, and pump array P7 can be designed to hold the contents of P0-P5 plus pump array P6. As described herein, this architecture can facilitate both multi-component (e.g., six component) mixing and magnetic bead-based DNA purification.

The modular nature of DPM chip architecture provided herein can facilitate multi-processor chips in which multiple Central Processors share common I/O rails. Such devices can enable, for example, parallel processing of multiple samples (e.g., four, eight, sixteen samples) samples on a single chip.

Figure 15:
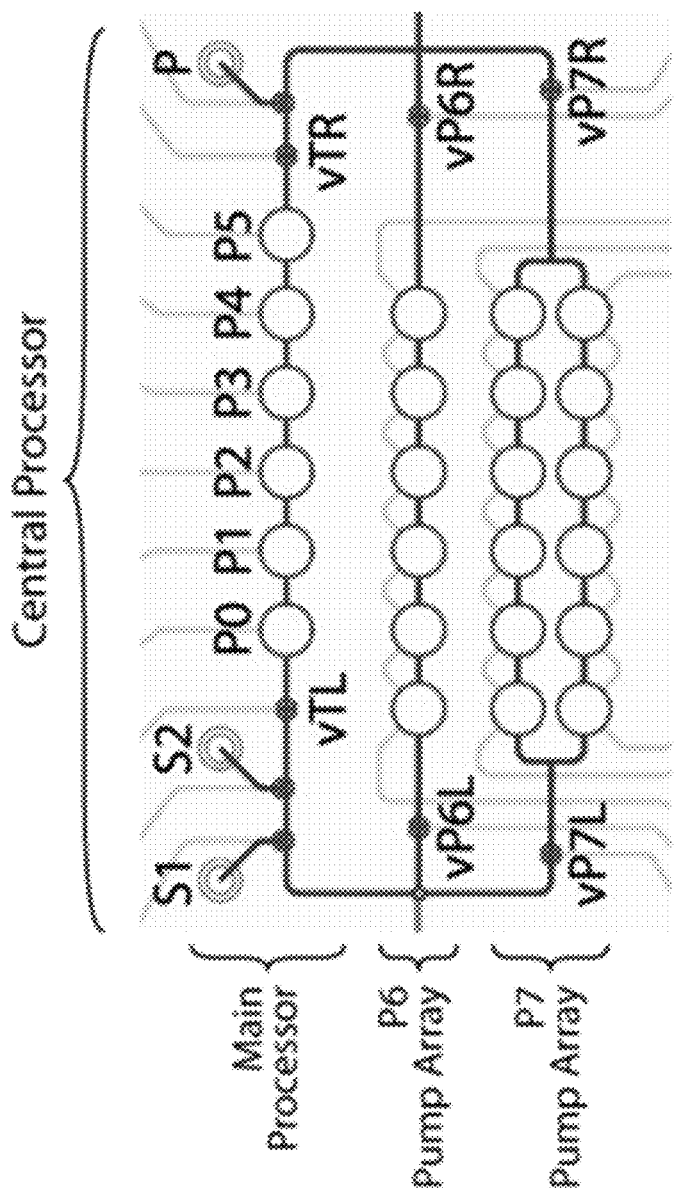
FIG. 15 schematically illustrates the central processor of the chip shown in FIG. 14.

Priming can be performed on the chip shown in FIG. 14 and FIG. 15. Priming is a preparation procedure that can be used for distinct activities that are frequently performed at the same time, such as, for example, (i) elimination of air, and (ii) washing of chip channels, valves, and pumps. The first activity, elimination of air, can be important when reagents and samples are first pumped into the chip from their respective reservoirs, as the chip is initially filled with air, which may be displaced. The second activity, washing, minimizes cross-contamination of reaction components and products, which may remain in chip channels, valves, and pumps after a given step is completed. A reagent or sample can be primed by repeatedly pumping it from its reservoir to a waste reservoir in another chip location. For example, referring to FIG. 14, a reagent in L1 may be primed by pumping it into P0, transferring it from P0 to P5, and then out to R1. Alternatively, if the main processor carries a reaction product that cannot be discarded, a reagent in L1 can still be primed by pumping the contents of P0 back to a different reservoir in the left rail.

Figure 16:
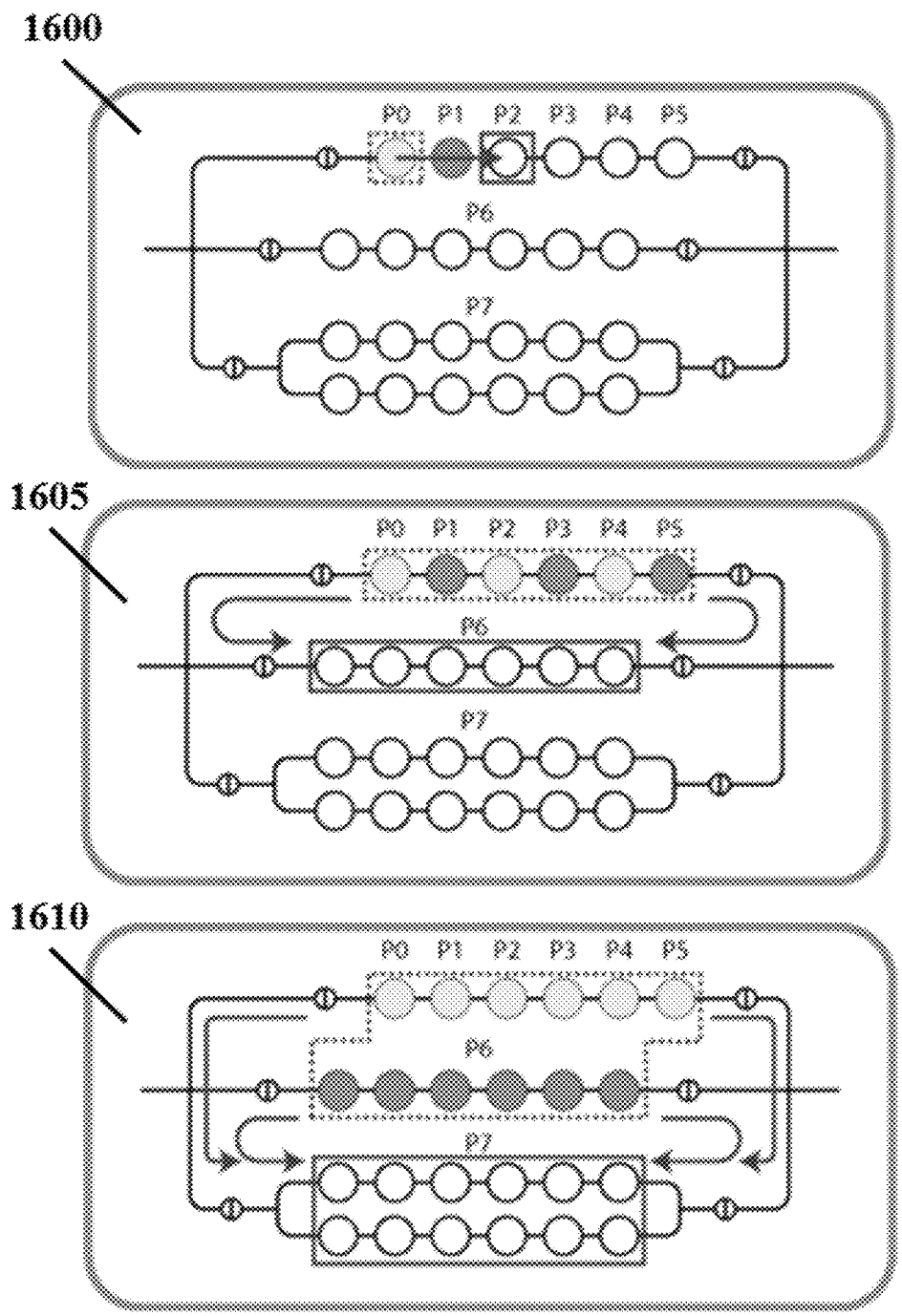
FIG. 16 schematically illustrates three digital mixing procedures.

Fluid transfer and mixing can be performed on the chip shown in FIG. 14 and FIG. 15. DPM devices can process discrete (digital) fluid volumes defined by each of the identical "single volume" pumps P0-P5. FIG. 16 shows three example digital mixing procedures including, 1:1 single volume mixing 1600, Six Volume mixing 1605, and Twelve Volume mixing 1610. Dotted boxes indicate pump closing and solid boxes indicate pump opening (filling). Arrows indicate the direction of fluid flow. Reagent is shown with dark gray fill of the pumps and sample with light gray fill of the pumps.

With reference to FIG. 14, FIG. 15 and FIG. 16 (at 1600), an example mixing procedure is described. For example, if a reagent resides in L1 and a sample (e.g., a nucleic acid sample) in S1, the reagent and sample can be mixed. In such cases, all pumps and valves can be initially closed and, the following program can be used to mix volumes (e.g., equal single volumes) of a reagent with a sample, where after each step of the program, normally closed valves (but not pumps) can be reset to the closed state: (i) the reagent can be loaded by opening L1's control valve, vTL, and P0 resulting in suction generated by P0 pulling the reagent from L1 into P0; (ii) the reagent can be moved by closing P0 and opening P1 resulting in reagent in P0 being simultaneously expelled from P0 and transferred into P1; (iii) sample is loaded by opening S1's control valve, vTL, and P0 resulting in suction generated by P0 pulling sample into P0 (sample and reagent now reside in adjacent pumps P0 and P1); and (iv) mixing can be performed by closing P0 and opening P2, then closing P1 and opening P3, then closing P2 and opening P4, then closing P3 and opening P5, resulting in sample in P0 being pushed through P1 into P2, resulting in mixing of sample and reagent. Mixing can be repeated any number of times (e.g., 2, 3, 4, 5, 6, 7, 8, 9, 10 or more times). As can be appreciated, the example program above may be utilized to mix any two fluids, including two reagent fluids and two sample fluids. Moreover, the mixing procedure described above can be extended to up to five individual components and/or pump volumes.

As illustrated in FIG. 16 (at 1605), mixing of six components/pump volumes can be accomplished with the use of Pump Array P6. Pump Arrays P6 and P7 can function as unified 6×- and 12×-volume pumps, respectively. P6 can permit the contents of P0-P5 to be mixed by reciprocal transfer between P0-P5 and P6. Similarly, in another example, Pump Array P7 can be used to perform 1:1 mixing of two six volume components, residing initially in P0-P5 and Pump Array P6, respectively. For example, this modality can be used to purify a species from a six volume reaction mixture residing in P0-P5 using, for example, PEG and/or NaCl buffers. With respect to the scheme illustrated in FIG. 16 (at 1610), a nucleic acid can be purified by: (i) loading an equal volume of magnetic bead slurry (e.g., six pump volumes of magnetic beads in 2× bead binding buffer) into P6; and (ii) mixing the magnetic beads in P6 and the nucleic acid in P0-P5 by reciprocal pumping between P0-P5, Pump Array P6 and Pump Array P7. Once mixing is complete, the magnetic beads can be captured in P5 by sequentially pumping the mixture through P5 to a waste port in the right-hand reagent rail while a high-strength magnet is positioned under P5.

Under the example chip architecture described above, a single volume mixing mode can utilizes up to five (single) pump volumes in the main processor to mix five different components at a 1:1 ratio, or fewer components at different ratios (1:1, 1:2, 1:3, etc.), by filling the appropriate number of pumps with a given component. The Single Volume mixing modality is flexible enough to provide mixing for most nucleic acid processing reactions such as those for end-repair, ligation, or A-tailing. It is also sufficient for execution of protocols that chain together consecutive reaction (e.g., up to four consecutive reactions) that increase in volume with each step. In another example, a six volume mixing modality can extend this flexibility to five consecutive reactions and a sixth mixed volume by utilizing Pump Array P6. Lastly, as described herein in another example, a twelve volume mixing modality utilizing Pump Array P7 can be used to facilitate nucleic acid purification with magnetic beads, starting from a six volume reaction.

Figure 17:
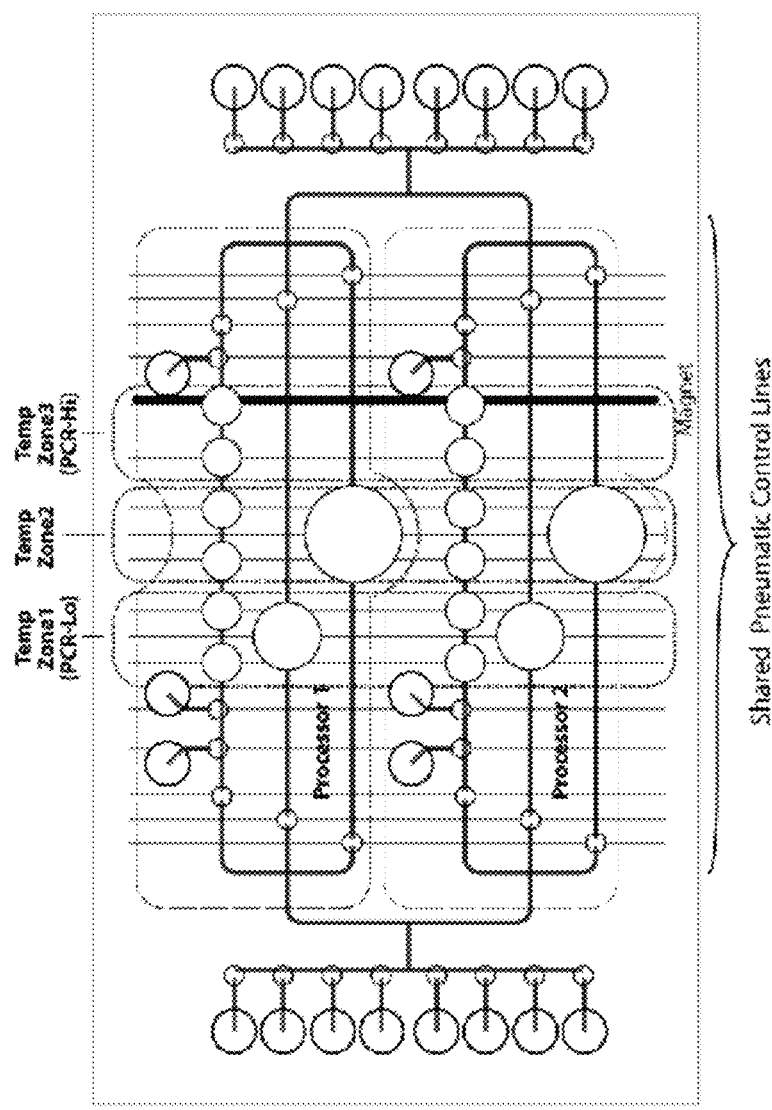
FIG. 17 schematically illustrates two central fluid processors sharing the same rails and pneumatic control channels.

FIG. 17 illustrates an example DPM chip having parallel central fluid processors and how two (or more, such as 3, 4, 5, 6, 7, 8, 9, 10 or more) central fluid processors may share the same rails and pneumatic control channels. In this case, multiple fluid processors can operate in lock-step for identical parallel processing of multiple input samples. For proper operation of the example DPM chip shown in FIG. 17, two (non-interacting) levels of pneumatic control channels are required (not shown).

Figure 18:
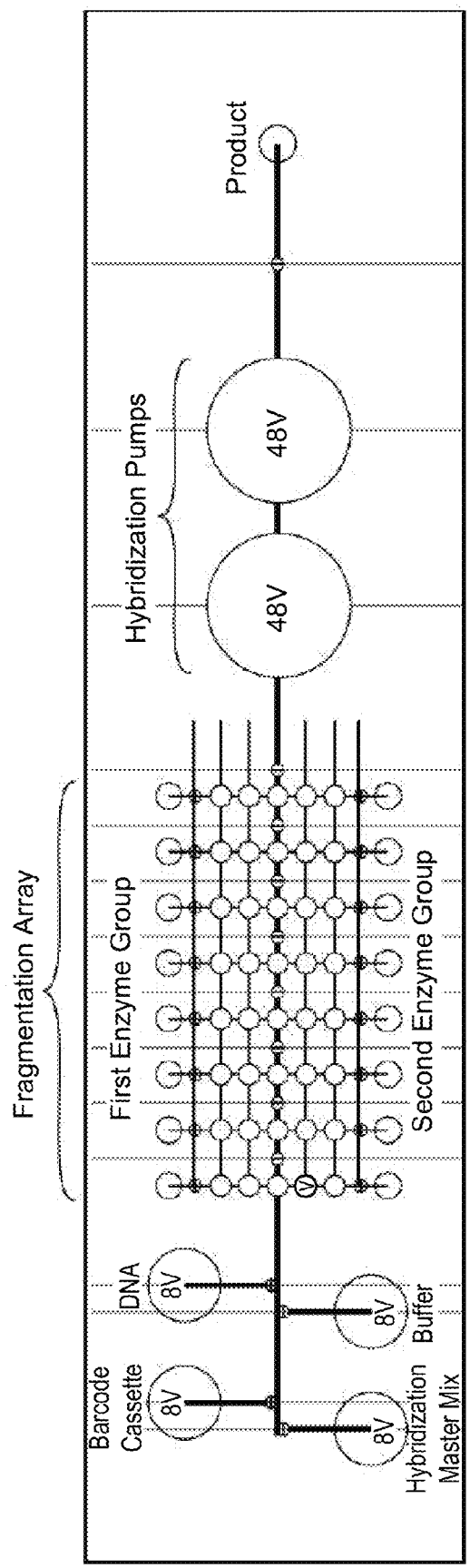
FIG. 18 schematically illustrates a highly parallel microfluidic architecture that can be suitable for performing eight distinct reaction incubations on an input sample, followed by reaction pooling (e.g., parallel-to-serial conversion) and extended incubation (e.g., nucleic acid hybridization)

FIG. 18 shows an example of parallel-to-serial reaction conversion and a schematic for an example highly parallel microfluidic architecture that may be suitable for performing eight distinct reaction incubations on an input sample, followed by reaction pooling (e.g., parallel-to-serial conversion) and extended incubation (e.g., nucleic acid hybridization). Each of the eight reactions can comprise: reaction buffer, nucleic acid, a first enzyme, and a second enzyme. The example configuration shown in FIG. 18 can be used, for example, to perform a fragmentation step with sixteen different restriction enzymes (eight first enzymes and eight second enzymes).

Microfluidic System

Figure 19:
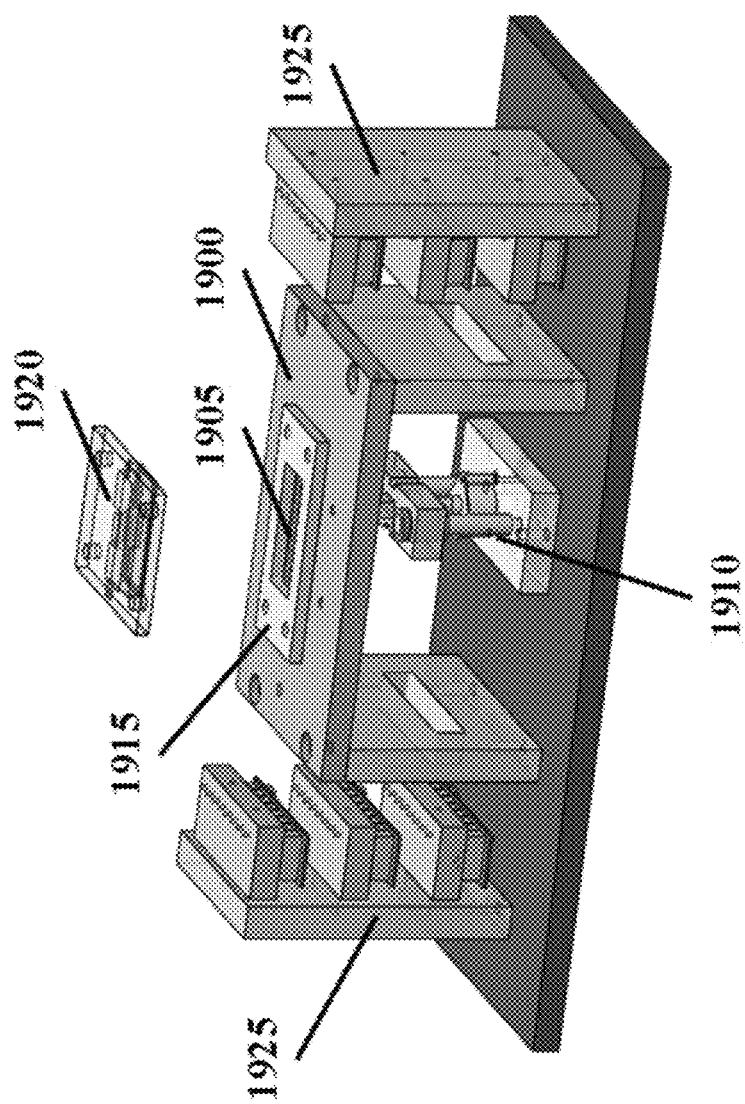
FIG. 19 schematically illustrates a breadboard system for operation of a chip.
Figure 20:
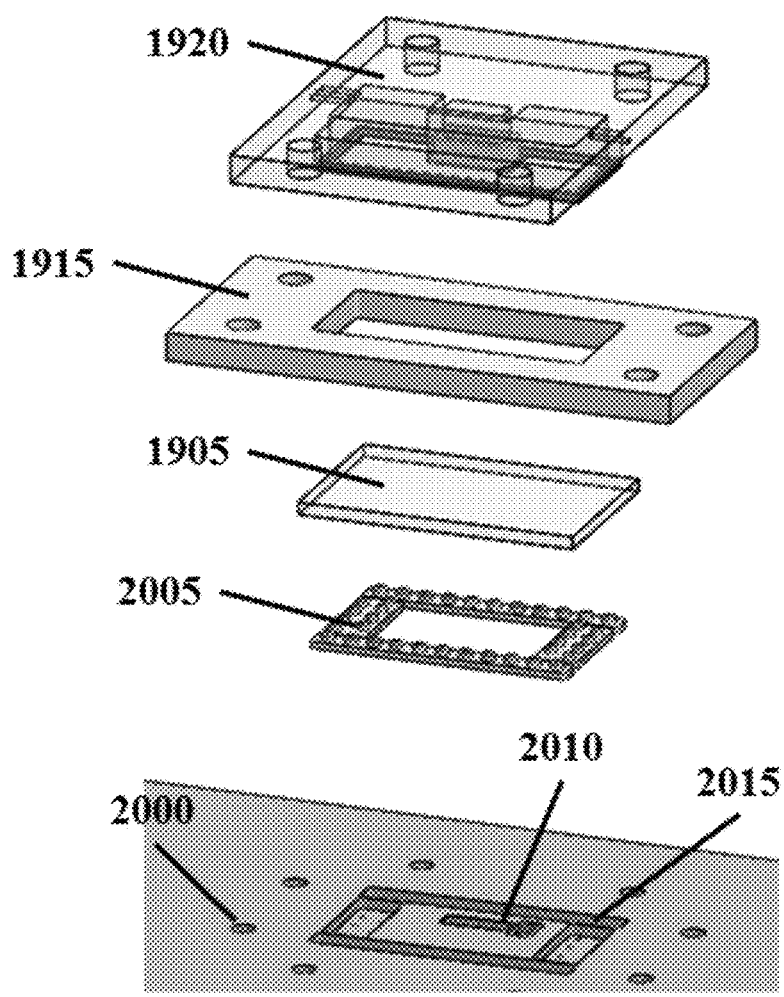
FIG. 20 schematically illustrates an exploded view of a chip interface.

As described herein, DPM chips can be actuated by positive pressure (to close) and vacuum (to open) pumps and valves. In addition and with respect to the example device shown in FIG. 14: (i) main processor pumps P0-P4 can be temperature controlled for thermocycling (and other temperature-dependent reactions), and (ii) a high-strength magnet can be moved in and out of contact with the bottom side of the chip to facilitate collection of magnetic beads in P5. FIG. 19 and FIG. 20 schematically depict an example system capable of receiving a DPM chip described herein and its components, where like numerals depict like elements. The system can be built on an aluminum base manifold 1900, which mates with the bottom surface of the chip 1905. As shown in FIG. 20, the base manifold carries through-holes 2000 and pockets for gaskets 2005 that make air-tight seals with the chip's bottom side pneumatic ports.

The base manifold 1900 can also comprises a pocket accommodating a heater 2010, and a through-hole for a movable magnet 2015, vertically positioned by an actuator 1910. The chip 1905 can be compressed onto the gaskets 2005 by an aluminum bezel 1915 via bolts and thumb screws (not shown). Finally, a removable transparent polycarbonate top manifold 1920 carrying an air-tight sealing gasket and transparent indium tin oxide (ITO) heater, may be placed in contact with the top side of the chip 1905. As described below, the top manifold can be used for thermocycling. Pressure and vacuum can be routed to chip pumps and valves via computer controlled solenoid valves 1925 mounted on either side of the base manifold. The solenoid valves 1925 can be connected to the bottom side of the manifold via flexible tubing (not shown). In addition to selecting between positive pressure and vacuum, solenoid valves 1925 can be connected to, for example, P4 and P5 as depicted in FIG. 14, and can switch between two different flow restrictors (not shown) to control the rates at which these pumps transition between open and closed states. Positive pressure and vacuum can be provided from a separate pump box (not shown). The chip can be operated at appropriate positive pressure (e.g., 30 psi positive pressure) and appropriate negative pressure (e.g., −13.5 psi vacuum) levels.

Figure 21:
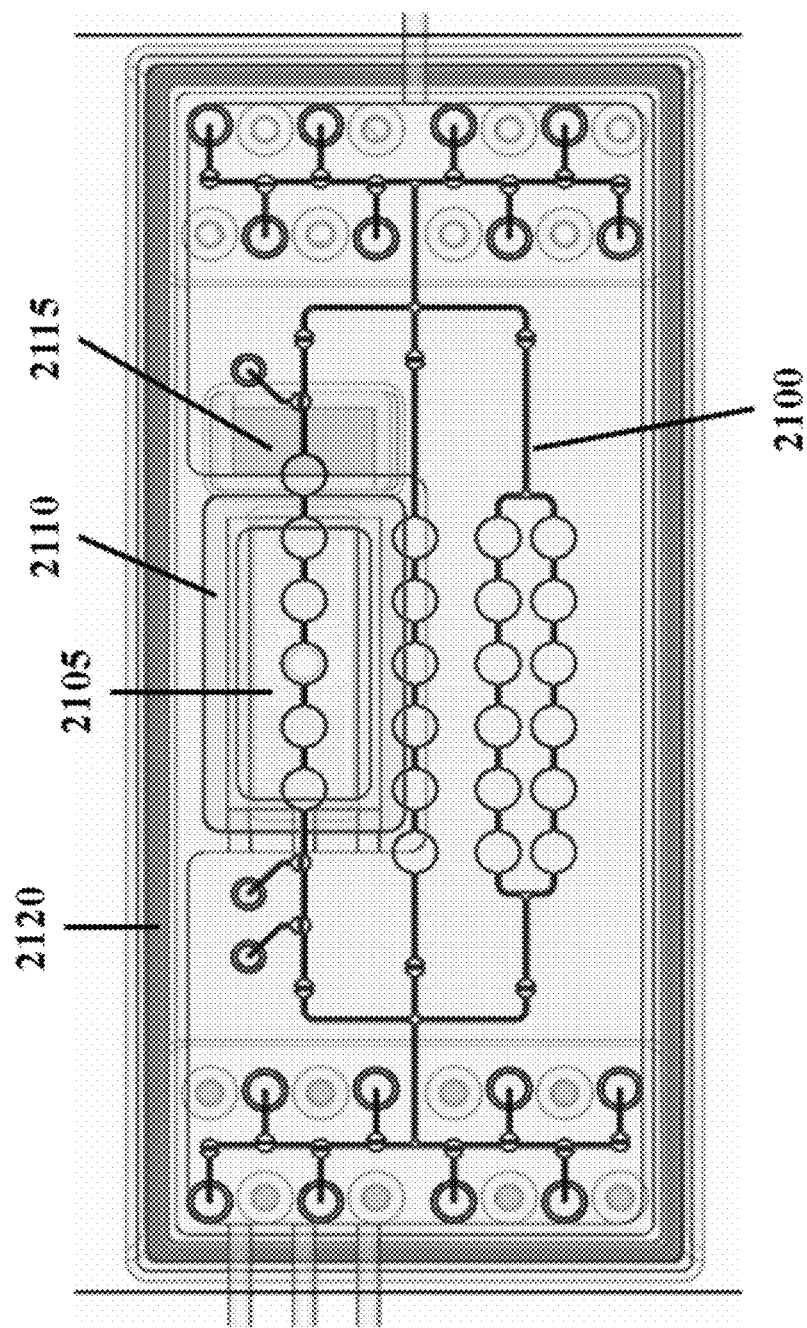
FIG. 21 schematically illustrates the assembled system through the top manifold.
Figure 22:
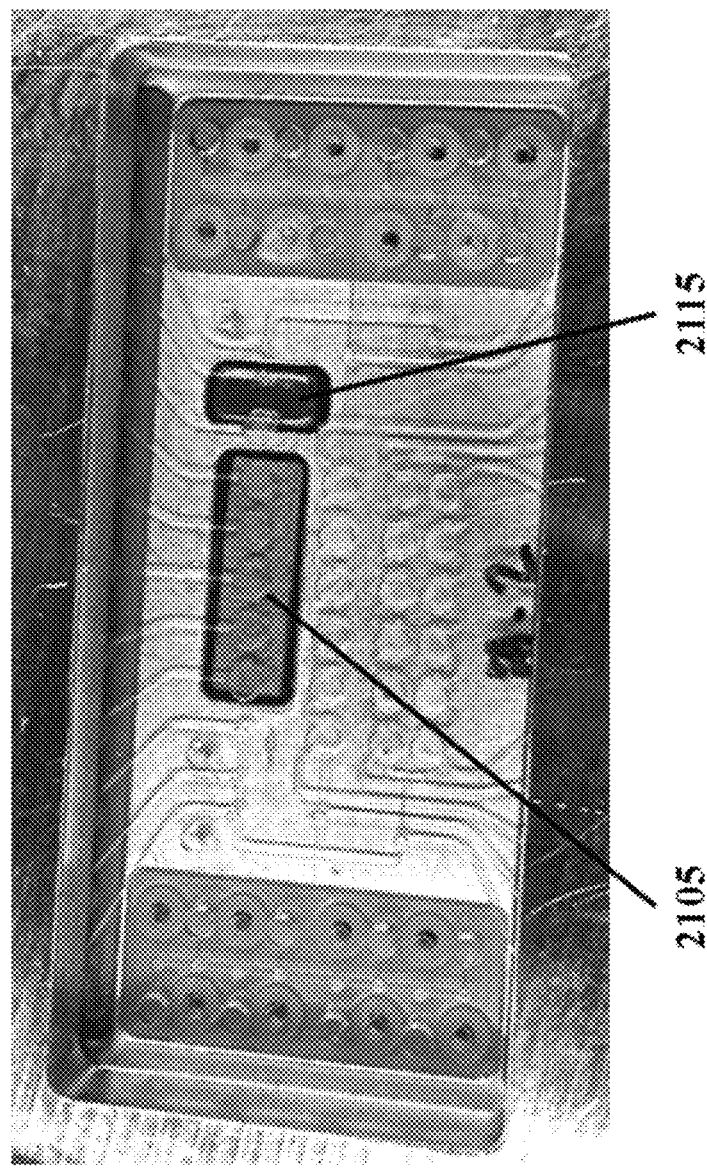
FIG. 22 is a photograph of the assembled system through the top manifold.

FIG. 21 and FIG. 22 show a top view of the chip when in the example system, with like numerals depicting like elements. In FIG. 21, the fluidic channels of the chip are depicted as black lines 2100. The chip can include top and bottom heaters 2105 are that can be positioned over and under pumps P0-P4, respectively and sealed with a gasket 2110. Moreover, a shielded magnet 2115 can be positioned so that its left edge is at the center of P5 for collection of magnetic beads. The bottom side heater assembly 2105 can be visible beneath one or more pumps (e.g., pumps P0-P4 as shown in FIG. 14), top manifold removed). The top and bottom side heaters can be any suitable heater. For example, the bottom side heater can be a stack comprising (from top to bottom): a copper heat distribution block (with thermocouple), a serpentine heater PC board, a polycarbonate spacer block, and a layer of closed cell foam to provide vertical compliance. The thermocouple and PC board heater wires can feed vertically down through small holes in the base manifold. In another example, the top side heater may be an Indium Tin Oxide (ITO) heater. Such a top side ITO heater can comprise a glass or sapphire substrate coated on the back side with a thin transparent ITO conducting film and metal electrodes. A small thermocouple (not shown) can be glued onto its back side, and the thermocouple and heater wires (not shown) can exit the top manifold to through air-tight feed-thrus. The two heaters, providing two sided heating to the chip (e.g., for fast thermocycling), can be controlled by two programmable proportional-integral-derivative (PID) controller and H-bridges connected to a computer. The controllers can be calibrated with chips carrying internal thermocouples that measure internal chip temperatures.

The top manifold can be pressurized during heating (e.g., thermocycling) to minimize temperature-induced growth of gas bubbles. Pressurization can be accomplished via a fitting on the right side of the top manifold, and a rectangular sealing gasket 2120 can maintain an air tight seal with the top surface of the chip. System components, such as solenoid valves, magnet actuator, and heaters can all be controlled by a computer. In some cases, the computer may run LabView software that includes a script interpreter capable of reading text files containing commands for solenoid valves and chip subsystems.

Additional features of the methods, valves, chips and/or systems of the present disclosure include: (i) minimized valve leakage and pump/valve dead volumes, (ii) minimized TPE film creep and/or adhesion (e.g., during thermocycling), (iii) minimized bubble generation (e.g., during thermocycling), (iv) on-chip reagent storage, and (v) reliable NGS library preparation involving multiple enzyme reactions, magnetic bead-based nucleic acid purification, and thermocycling.

A membrane valve and pump function can depend on a complex interplay of feature geometry and the viscoelastic properties of the elastomer membrane, which in turn can depend on its chemical composition, fabrication conditions (in this case extrusion), thickness, and service temperature. In particular, the degree to which a valve or pump seals or closes (respectively) can depend on the degree to which the elastomer film conforms to the mating features of the valve or pump fluidic-side body (e.g., a dome in the case of normally open valve, or a valve seat in the case of a normally closed valve). For any given membrane film modulus, this can depend on the vertical deformation distance (feature depth), valve body diameter (larger diameters producing less stress), and/or film thickness (thinner films requiring less force to deform). Design of membrane valves and pumps can be guided by finite element modeling (FEM), however accurate simulation can depend on the existence of accurate material parameters (e.g., storage modulus, loss modulus, and tan delta ($\delta$)) which can be determined for each new elastomer composition, such as, for example, by Dynamic Mechanical Thermal Analysis (DMTA).

The design of DPM chip valves and pumps can be optimized for (i) functional yield, (ii) minimization of leakage and dead volumes, or for (iii) high temperature film operation. Factors (ii) and (iii) can both affect performance during thermocycling. For example, leakage can prevent maximum pressurization of thermocycled pumps (e.g., P0-P4 as shown in FIG. 14), and film malfunction at high-temperature can disable pumps. With respect to (iii), considerable temperature-induced creep (permanent deformation) may cause pump malfunction during (and after) thermocycling. Similarly, increased COP-TPE adhesion during thermocycling can render pumps inoperable due to effectively irreversible adhesion to pump body structures in either open or closed states. In particular, the softening of the hard styrene component of SEBS TPE (e.g., at 95° C.) can play a role in promoting both creep and adhesion in this temperature range.

As noted herein, facile chip assembly is one key advantage of the devices described in the present disclosure. In some cases, adhesion of TPE films to low surface energy thermoplastics such as COP can be promoted by increased lamination temperature, pressure, and time, all of which can promote closer molecular association, and in some cases inter-diffusion, of the two surfaces. In addition, surface preparation by UV-ozone (UVO) treatment has opposite effects on adhesion of COP surfaces and TPE films, with increased UVO exposure of COP surfaces increasing COP-TPE adhesion, and increased UVO exposure of TPE film surfaces decreasing COP-TPE adhesion. To optimize yield, COP-TPE adhesion can be characterized as a function of (a) UVO treatment time (e.g., between about 0 min and about 10 min), and (b) lamination temperature (e.g., between about 25° C. and about 250° C.), pressure (between about 1 PSI and about 50 PSI), and feed rate (between about 10 mm/min and about 100 mm/min). Overall chip bonding quality can be qualitatively assessed by (i) the number and size of any voids or air pockets in the bonded sandwich after lamination, (ii) the force required to manually pry apart the assembled chip, (iii) the force required to peel the TPE film off from a COP surface (peel test), and (iv) the number of stuck (non-functional) valves and/or pumps.

Pump and valve geometries can be optimized. Fluidic and pneumatic layers can be designed and fabricated with a range of valve and pump body shapes (flat, dome), depths (e.g., from about 100 µm to about 250 µm), diameters (e.g., from about 0.5 mm to about 2 mm), valve seat widths (e.g., from about 100 µm to about 300 µm) and valve seat surface recess distance (e.g., from about 0 µm to about 50 µm). These can be assembled into chips with TPE films of varying composition and thickness, as described herein. Prior to assembly, injection molded pump, valve, and channel features can be inspected using, for example, a microscope (e.g., a 3D Optical Profiling microscope (Zeta-20 Optical Profiler)), which can ensure that 3D CAD model geometries are accurately translated into actual feature geometries by the mold-making (CNC machining) and injection molding process.

Valves and pumps in assembled devices can be characterized at room and thermocycling temperatures (e.g., from about 60° C. to about 95° C.) for leakage and dead volumes. Qualitative performance (leakage and unswept dead volumes) can be readily observed with food dye under low power magnification. Leakage can be quantitatively characterized by measuring flow rates through closed pumps and valves as a function of applied fluid pressure. For example, effective unswept dead volume can be quantitatively characterized by measuring mixing ratio of a DNA solution and TE mixed under 1:1 conditions. This can be accomplished by measuring the initial and final DNA concentrations using a double-strand DNA specific fluorescent (Qubit) assay.

In some embodiments, a TPE film is suitable for operation at high temperatures. For example, the maximum service temperature of SEBS TPEs can be determined by the melting temperature of the styrene (hard) component, which is approximately 95° C. (glass transition temperature, $T_g$). In some cases, this is not sufficient for thermocycling applications, which routinely denature nucleic acids at temperatures of between about 95° C. and about 99° C. The properties of SEBS TPEs can be modified, for example, by (i) blending with other polymers such as random copolymer polypropylene (rcPP, $T_g$=134° C.), and (ii) by e-beam-induced crosslinking To accomplish (i), TPE films containing varying amounts of rcPP (e.g., about 0%, 5%, 10%, and 15% by weight) can be created at varying thicknesses (e.g., about 100 µm or 250 µm). To accomplish (ii), films can be exposed to e-beam radiation at doses of about 60 to about 240 kilogray (kGy). In addition, non-SEBS TPE materials can be used, such as thermoplastic urethanes (TPUs).

The performance of chip pumps during thermocycling can be qualitatively monitored by visual inspection of pump activity, and quantitatively monitored by determination of the fluid volume remaining in the pump(s) after thermocycling. Temperature-induced creep can be assessed by disassembling thermocycled chips and inspecting film surfaces for any significant deformation (e.g., having a feature height >10 µm), such as, for example with a microscope (e.g., a Zeta-20 optical Profiling microscope). Excessive adhesion in pumps and valves can be characterized by observation of valve and pump function during thermocycling followed by disassembly of chips to determine the amount of creep. Moreover, shadow masked UVO (or other plasma) treatment can be used, and/or selective application of Teflon AF (liquid Teflon) to TPE films and/or pump bodies can be used, for selective decreased COP-TPE adhesion under thermocycling conditions. Moreover, a DMTA instrument (e.g., a Q800 DMTA instrument) can be used to characterize the temperature-dependent mechanical properties of the films, and model valve and pump function using accompanying software, such as, for example SolidWorks FEM software.

In one example, a pump can operate normally after up to 40 thermocycles with (chip-internal) temperature profile: 95° C. for 2 min, followed by 40 cycles of 95° C. for 10 sec, 60° C. for 1-10 min cycling.

In some embodiments, gas bubbles do not form during thermocycling in the microfluidic chips of the present disclosure. Temperature-induced nucleation of gas bubbles can be minimized. Bubble initiation temperature (e.g., onset of nucleate boiling, ONB) can be a function of ambient pressure, solute composition, dissolved air, the presence of insoluble (debris) particles, and the physical properties of the walls of the container. These factors can be optimized to minimize bubble formation.

Figure 29:
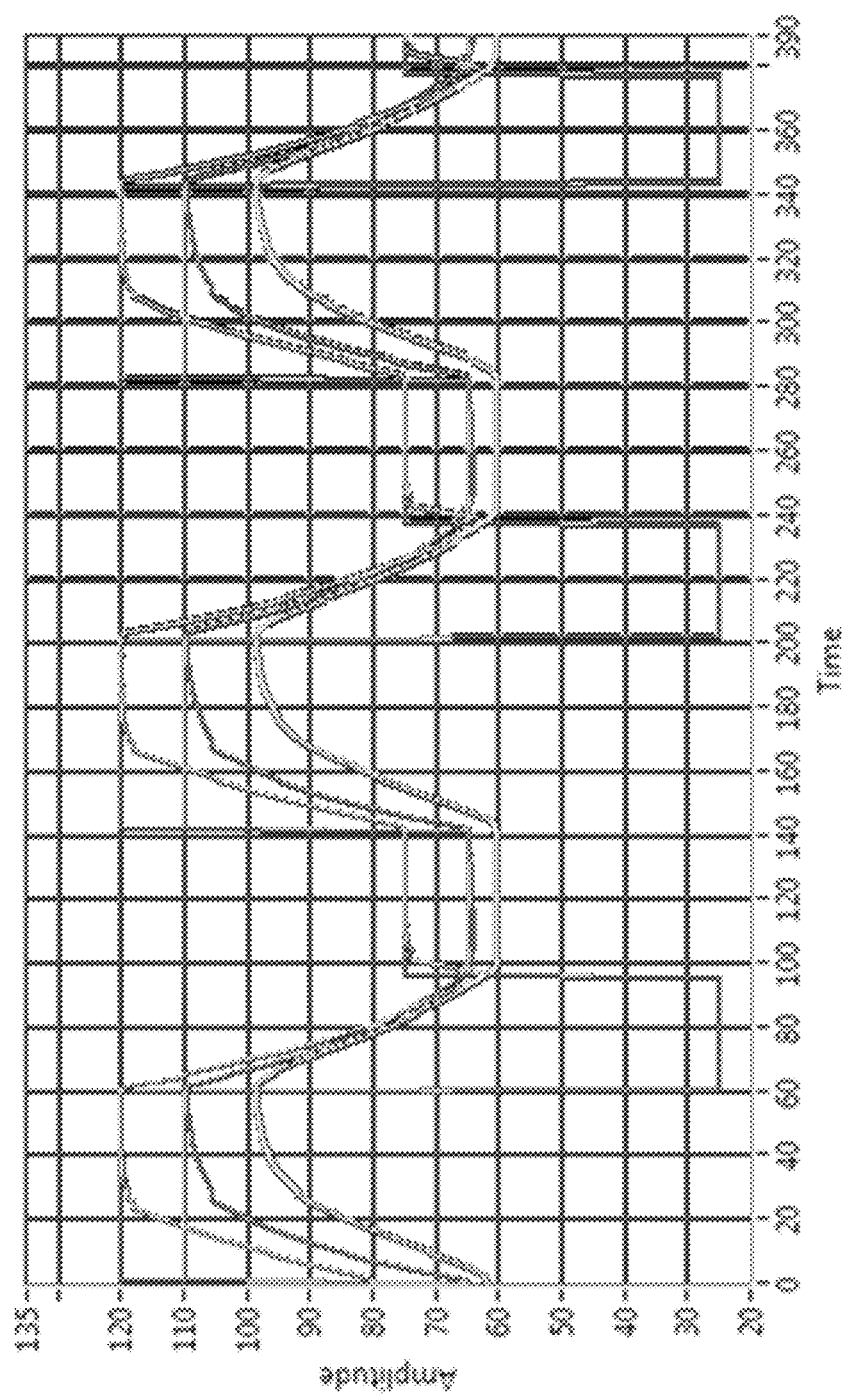
FIG. 29 shows an example of PCR reaction in a DPM chip of the present disclosure.

In some cases, bubbles can grow rapidly at temperatures above approximately 75° C. Minimization of the time reactions spend between 75° C. and 95° C. can minimize bubble formation. FIG. 29 shows an example that depicts, in some cases, the top and bottom heaters require approximately 30 seconds to transition from their annealing to their denaturation temperatures. This time can be limited by the maximum power dissipated by the heaters. In addition, a heater can be designed for maximum power dissipation. In contrast, the time required for cooling can be determined by passive heat transfer from the thermal mass of a heated chip region.

Expansion of trapped air from microscopic unwetted particle/container surfaces, as well as nucleation of water vapor bubbles, can be promoted by surface roughness on the order of 1-10 microns. Combined with the substantial hydrophobicity of the TPE film and, for example, a COP fluidic valve body, these irregularities may trap air micro-bubbles that can both expand and promote nucleation of water vapor bubbles at thermocycling temperatures. Therefore, surfaces of the devices of the present disclosure can be designed to be smooth, with roughness of less than about 10, less than about 5, less than about 1, less than about 0.5, less than about 0.1, less than about 0.05, or less than about 0.01 microns.

Moreover, bubble formation at thermocycling temperatures can be reduced or eliminated by (a) modulating temperature transition times, (b) modulating wetting and solutes, (c) modulating feature smoothing, or (d) using an active debubbler.

For minimization of heating times, the maximum power dissipation limits of the top and bottom heaters can be determined, and operated at or near their respective limits. If the transition times cannot be substantially reduced due to current density limitations, the heaters can be designed to have increased cross-section conductive paths (e.g., copper trace thickness and width for the bottom PCB heater, and thicker ITO film for the top heater). For minimization of both heating and cooling times, the effective thermal mass (heat capacity) of the chip can be reduced by reducing the thickness of the COP fluidic and pneumatic layers (e.g., by approximately 50%) and/or by milling out rectangular sections on the external surfaces coinciding with one or more pumps (e.g., pumps P0-P4 as shown in FIG. 14), in both layers. In addition, the thermal performance of chips incorporating reduced thickness (e.g., 100 µm rather than 250 µm) TPE films can be evaluated. SolidWorks FEM modeling of the thermal system can, for example, guide such optimizations.

Surfactants with hydrophilic-lipophilic balance (HLB) in the 6-10 range can function as wetting agents that can minimize air retention on hydrophobic chip surfaces. Thermocycling performance can be evaluated with surfactants such as Span20 (HLB=8.6), Span40 (HLB=6.7), Brij52 (HLB=5.3), and BrijL4 (HLB=9.0) with their thermocycling compatibility characterized under static and dynamic coating conditions. For static coating, for example, 1% surfactants in 80% EtOH can be pumped into the a main processor and annealed near the TPE Tg (95° C.-134° C.) for several hours before thermocycling testing. For dynamic coating, surfactants can be added directly to buffer (e.g., at final concentrations ranging from 0.01% to 1%). In addition, high boiling point thermocyling-compatible reagents such as glycerol and PEG can be added to thermocyling buffers to raise their boiling points and prevent bubble formation.

In some cases, increased mold feature smoothness can increase the maximum (bubble-free) chip operating temperature by creating chip molds with increasing levels of feature smoothness by (i) machining with alternative patterns/rasters and reduced step sizes, (iii) polishing, and (iv) nickel coating (e.g., films thickness 10 to 25 µm).

In some cases, a chip can have an active degassing/debubbling capability by equipping pumps (e.g., pumps P0-P4 shown in FIG. 14) with a hydrophobic membrane. For example, a hybrid Teflon AF-PDMS membrane can provide effective gas removal under thermocycling conditions with minimal water loss.

Implementation of the active debubbler can involve modification of the top manifold to provide (i) a gap between the top-side heater and membrane, and (ii) a vacuum-tight sealing interface (O-ring) to the top surface of the membrane, rather than positive pressure to the entire chip surface. The membrane can provide both degassing capability prior to thermocycling, and debubbling during thermocycling.

In some embodiments, a system of the present disclosure has (i) negligible visible displacement of nucleic acid amplification (e.g., PCR) reaction volumes over up to 40 amplification cycles with (chip-internal) temperature profile: 95° C. for 2 min, followed by 40 cycles of 95° C. for 10 sec, 60° C. for 1-10 min cycling, and (ii) amplification (e.g., PCR) product yields within 2× (one ideal nucleic acid amplification (e.g., PCR) cycle) of conventional thermocycler yields with the same reaction.

Pre-loaded reagent-equipped chips can provide significant reduction of user-burden. In some embodiments, enzymes and/or buffers, magnetic beads (e.g., slurries), and ethanol-containing wash solutions can be accommodated. This can be accomplished through exploitation of COP-TPE adhesion phenomena to create "semi-permanently closed" (SPC) valves. Incorporation of semi-permanently closed valves into the DPM chips of the present disclosure can prevent liquid reagents (deposited in chip reservoirs during manufacturing) from leaking prematurely into the chip channels during storage.

COP-TPE adhesion in valves can be manipulated by application of alternative temperature and/or pressure profiles. Therefore, a closed state can be stabilized so that it remains stable and leak-free for an extended period (e.g., up to one year) in the absence of applied control (positive) pressure, under a variety of ambient conditions. The so-called "semi-closed" state can be activated by application of a first pressure and/or temperature profile during manufacturing, and reversed by application of a second temperature and/or pressure profile when the chip is ready to be used. Reversal can be accomplished at run time in the instrument, for example, by positioning small, localized heaters (e.g., housed in the base manifold) in contact with the appropriate valves in the left and right reagent rails, applying vacuum to the pump control lines, and/or positive pressure to the reservoirs. Reversal can also be accomplished using the pin valves described herein.

Semi-permanently closed (SPC) states can be achieved with the TPE compositions and valve designs described herein. This can be accomplished by subjecting valves to closing and opening temperature and/or pressure profiles spanning: from about 25° C. to about 100° C., and from about 5 PSI to about 30 PSI for closing (and vacuum for opening), and application times of about 1 to about 24 hours (closing) and about 30 sec to about 5 min (opening). The SPC valve structures can provide (i) larger film-valve body contact areas and/or (ii) micropatterned (roughened) contact surfaces that increase contact areas and thereby enhance adhesion (e.g., roughening is readily provided by CNC machining marks on the mold). Also, closed states of SPC valves can be stabilized with either (i) localized increased UVO treatment of COP valve structures, and/or (ii) localized decreased UVO treatment of TPE films. This can be accomplished with the aid of shadow masks during UVO treatment. Finally, various TPE compositions, with and without tackifiers (e.g., C5 aliphatic and/or C9 aromatic hydrocarbon resins) can be used in SPC valves. The use of any such enhanced-adhesion TPE films, however, can require that chips be assembled with two different TPE film pieces, one for normal valve operation, and one with increased adhesion for SPC valves.

As a compliment or alternative to semi-permanently closed valves, dry reagents can be used in which enzyme solutions are lyophilized/freeze-dried in reagent reservoirs. The end-user then rehydrates the enzymes by adding water (or TE or ethanol wash solutions). Rehydration can be promoted by reciprocal pumping of added water into and out of reservoirs by high volume pump array (e.g., P7 array shown in FIG. 15).

In some cases, the devices described herein have on-chip storage of magnetic bead solutions. In some cases, 1 µm (or larger) diameter beads can settle in less than one hour, becoming packed and difficult to resuspend after approximately 24 hours. In some cases, long- and short-term settling can be reversed by (i) vortexing or agitating the chip prior to actuation, and/or (ii) high flow rate reciprocal on-chip pumping in-to/out-of the bead solution reservoir utilizing the high volume pump array (e.g., P7 array shown in FIG. 15). In some cases, (iii) the membrane underlying the bead reservoir is actuated (pneumatically or mechanically) such that packed beads can be repeatedly launched ballistically from its surface into solution.

Sequencing Library Preparation

Target enrichment is one of several NGS library preparation methods, and can be used for the sequencing devices and methods describe in PCT Patent App. No. PCT/US2011/054769, PCT Patent Application No. PCT/US2012/039880, PCT Patent App. No. PCT/US2012/067645, PCT Patent Application No. PCT/US2014/027544, PCT Patent Application No. PCT/US2014/069624 and U.S. patent application Ser. No. 13/481,858, each of which is entirely incorporated herein by reference. In some cases, a DPM chip can be used for Ion AmpliSeq™ target enrichment library preparation, which is described below as an illustrative example. An example Ion AmpliSeq™ protocol begins with a highly multiplexed PCR reaction of 11-21 cycles (depending on primer pool complexity) followed by partial digest (end-repair) and adapter ligation reactions without any intermediate purification and/or concentration steps. A total of seven enzyme and DNA components can be sequentially added to a growing reaction volume. The ligation reaction can be followed by an AMPure magnetic bead-based clean-up step. The washed and dried beads can then mixed directly into a second PCR reaction, which both amplifies the targeted sequences and adds additional "equalizer" sequences which can be used in a final normalization step. Normalization can rely on streptavidin-coated magnetic beads and limiting quantities of biotinylated DNA probes hybridizing specifically to the equalizer sequences of the amplicons to immobilize a defined quantity of the amplicon pool on the beads. After washing, the final, normalized amplicons can be dehybridized (eluted) from the beads in a TE-glycogen buffer.

Adaptation of an Ion AmpliSeq™ protocol (or any other protocol) to DPM processing can involve reduction of reaction volumes and adjustment of mixing ratios to quantized (digital) values such as 1:1, 1:2, etc. For example, an initial PCR reaction can comprises three component volumes: V(1) 4 μL 5× Ion AmpliSeq HiFi Mix, V(2) 4 μL 5× Ion AmpliSeq Primer Pool, and V(3) 12 μL DNA template. The final concentrations of the HiFi Mix and Primer Pool can be 1× in a 20 μL reaction volume. In the case of the DPM processing, processing can be described in terms of digital units, or pump volumes (V, 2V, 3V, etc.); V being the fluid volume contained in a single (open/filled) pump, which can be approximately 0.3 μL, for example. One-to-one mixing of V(1) and V(2) can result in 2V(1.2) (two volumes of components 1 and 2), both at half (2.5×) concentration. In some cases, one of these volumes can be discarded (pumped to a waste reservoir), leaving 1V(1.2). Addition of a single volume of the third component (template DNA) can then result in two volumes of the complete reaction, 2V(1.2.3), in which the reagent concentrations (1 and 2) are halved again to 1.25×. Thus in this example, the final concentrations of HiFi Mix and Primers are 25% higher than in a bench protocol. These final concentrations can be adjusted downward to 1× by pre-dilution of the two reagents (from 5× to 4×) with appropriate buffers, rendering DPM processed reactions in the above example chemically identical to a bench reaction with three exceptions.

In the first exception, the final DNA template concentration was reduced from 1× to 0.83×. Second, the reaction volume was reduced from 20 μL to 0.6 μL. Third, the primer (pool) mass, polymerase mass, and dNTP mass were all been reduced by a factor of approximately 25 (4/0.15=26.7). Accordingly, the maximum possible quantity (mass) of amplification product (amplicons) was also reduced by a similar factor.

In some cases, right and left I/O rails of a DPM chip, can hold a plurality of Ion AmpliSeq™ reagents (e.g., up to thirteen), as well as providing waste (left rail) and waste and air (right rail) reservoirs. DNA reagents specific to each sample (e.g., sample DNA and barcoded adapter) can each be input to processor-specific reservoirs (e.g., S0 and S1 shown in FIG. 14), and the product can removed from an output reservoir (e.g., P shown in FIG. 14).

Integration DPM Chip with Sensor Chip

The microfluidic valves and devices of the present disclosure can be integrated with one or more sensor chips. The microfluidic valves and devices of the present disclosure can provide and/or remove one or more fluid species to/from the sensor chip. Moreover, microfluidic valves and devices provided herein may prepare samples and/or reagents for reactions and/or sensing of such reactions in a sensor chip. Accordingly, a sensor chip may comprise one or more fluidic channels capable of receiving/outputting one or more fluid species from microfluidic valves and devices described herein Such fluidic channels can be fluidly connected to microfluidic valves and devices of the present disclosure. Moreover, a DPM chip as described herein may include one or more sensor chips. Such a sensor chip may be a fixed, permanent feature of a DPM chip (e.g., not removable from the DPM chip) or may be an addable/removable feature.

Examples of sensor chips are described in PCT Patent App. No. PCT/US2011/054769, PCT Patent Application No. PCT/US2012/039880, PCT Patent App. No. PCT/US2012/067645, PCT Patent Application No. PCT/US2014/027544, PCT Patent Application No. PCT/US2014/069624 and U.S. patent application Ser. No. 13/481,858, each of which is entirely incorporated herein by reference.

A sensor chip may comprise one or more sensors that may be arranged in an array, such as a sensor array. A sensor array may comprise a substantially planar substrate comprising a plurality of sensors. In some cases, a sensor may comprise one or more of the same electrodes and/or different electrodes. In some cases, a sensor may comprise a pair of electrodes. A sensor(s) (e.g., via electrodes) may be used to detect one or more species (e.g., nucleic acids, proteins, antibodies, peptides, small molecules, etc.) and/or reactions of interest, such as nucleotide incorporation during a primer extension reaction associated with a nucleic acid sequencing reaction. Other examples of reactions of interest include a receptor-ligand binding reaction, an antibody-antigen binding reaction, a nucleic acid hybridization reaction, a protein-protein interaction, an enzymatic reaction, etc. A sensor may be any suitable type of electrical or optical sensor capable of sensing a species and/or reaction of interest. In some cases, a sensor (e.g., a NanoBridge sensor) may function as a pH or charge sensor, with examples of such sensors described in U.S. Published Patent Application No. US 2012/0138460, titled "BIOSENSOR DEVICES, SYSTEMS AND METHODS THEREFOR", which is incorporated herein by reference in its entirety for all purposes. Such a sensor may detect a change in pH (e.g., local pH change) or change in charge (e.g., change in local charge) associated with a species and/or reaction of interest.

In some cases, a sensor (e.g., a NanoNeedle sensor) may function as a charge, conductivity and/or impedance sensor. Such a sensor may detect a change in charge (e.g., local change in charge), change in conductivity (e.g., local change in conductivity), change in impedance (e.g., local change in impedance) associated with a species and/or reaction of interest. Examples of such sensors are described in PCT Patent Application No. PCT/US2011/054769, PCT Patent Application No. PCT/US2012/039880, PCT Patent Application No. PCT/US2012/067645, PCT Patent Application No. PCT/US2014/027544, and U.S. patent application Ser. No. 13/481,858, each of which is incorporated herein by reference in its entirety for all purposes. In some embodiments, a sensor may function as a heat sensor or a capacitance sensor. Such a sensor may detect a change in heat (e.g., a local change heat) and/or a change in capacitance (e.g., a local change in capacitance) associated with a species and/or reaction of interest. As can be appreciated, a sensor may sense a species and/or reaction of interest via one or more characteristics, such as, for example, charge and impedance, conductivity and charge, conductivity and impedance, conductivity, charge and impedance and so on.

Sensing of a species and/or reaction of interest may be based on at least one of local pH change, local impedance change, local heat detection, local capacitance change, local charge concentration (or change thereof), and local conductivity change. In some embodiments, a sensor may sense a species and/or reaction of interest by sensing (e.g., detecting signals indicative of) a local conductivity change, local impedance change, local capacitance change and/or local charge concentration (or change thereof) of the species and/or one or more reactants or products of the reaction of interest. In some embodiments, a species and/or one or more reactants or products of a reaction of interest may be coupled to a carrier (bead, particle or other type of surface). In such cases, a sensor may sense the species and/or reaction of interest by sensing (e.g., detecting signals indicative of) a local conductivity change, local impedance change, local capacitance change and/or local charge concentration (or change thereof) of the carrier or species coupled to the carrier. In some embodiments, a carrier may be a magnetic carrier (e.g., magnetic bead or particle) that can be magnetically immobilized adjacent to or in proximity to a sensor during sensing. In some embodiments, a carrier may be a carrier that can be electrostatically immobilized adjacent to or in proximity to a sensor during sensing. In some embodiments, a species and/or one or more reactants or products of a reaction of interest may be coupled to a surface of a sensor. In such cases, a sensor may sense the species and/or the reaction of interest by sensing (e.g., detecting signals indicative of) a local conductivity change, local impedance change, local capacitance change and/or local charge concentration (or change thereof) of the sensor. In some cases, a sensor may sense a species and/or reaction of interest within the Debye length (e.g., Debye layer) of (i) the species or one or more reactants and/or products of a reaction of interest; (ii) a carrier associated with the sensor; (iii) a species or one or more reactants and/or products of a reaction of interest associated with a carrier or the sensor; and/or (iv) the sensor.

For example, a reaction of interest may be a nucleic acid sequencing reaction, such as, for example a sequencing-by-synthesis reaction. In such a sequencing-by-synthesis reaction, a template nucleic acid may be sequenced by hybridizing a primer to the template nucleic acid and extending the primer with nucleotides (e.g., incorporation of nucleotides to the template nucleic acid) in template-directed fashion via the action of a polymerase. A sensor of a sensor chip can sense nucleotide incorporation events as and/or after they occur, where signals obtained from the sensors can be used to generate a sequence for the template nucleic acid. Different nucleotides (e.g., nucleotides having a base comprising adenine (A), guanine (G), cytosine (C), or thymine (T)) can be contacted (e.g., flowed into the chip) with a template nucleic acid in sequential fashion, whereby each sensed nucleotide incorporation event can be identified as incorporation of a particular nucleotide.

Sensing of nucleotide incorporation events may be based on at least one of local pH change, local impedance change, local heat detection, local capacitance change, local charge concentration (or change thereof), and local conductivity change. In some embodiments, a sensor may sense nucleotide incorporation events by sensing (e.g., detecting signals indicative of) a local conductivity change, local impedance change, local capacitance change and/or local charge concentration (or change thereof) of a template nucleic acid to which nucleotides are incorporated. In some cases, a template nucleic acid may be coupled with a carrier (e.g., bead, particle or other type of surface). In such cases, a sensor may sense nucleotide incorporation events by sensing (e.g., detecting signals indicative of) a local conductivity change, local impedance change, local capacitance change and/or local charge concentration (or change thereof) of the template nucleic acid molecule and/or the carrier. In some cases, a template nucleic acid may be coupled with a surface of a sensor. In such cases, the sensor may sense nucleotide incorporation events by sensing (e.g., detecting signals indicative of) a local conductivity change, local impedance change, local capacitance change and/or local charge concentration (or change thereof) of the template nucleic acid molecule and/or the sensor. In some cases, a sensor may sense nucleotide incorporation events within the Debye length (e.g., Debye layer) of (i) a template nucleic acid, (ii) a carrier coupled to a nucleic acid template and in proximity to the sensor, (iii) a template nucleic acid coupled to a carrier or the sensor, and/or (iv) the sensor.

A sensor chip may be capable of combined nucleic acid amplification and nucleic acid sequencing. In some embodiments, such a sensor chip may comprise an array of sensors, wherein each position of the array comprises one or more features that can trap a carrier having a template nucleic acid at a given position of the array. For example, a sensor chip may comprise a magnetic array that can trap a magnetic bead or particle having a template nucleic acid by magnetic force at a plurality of the array positions. In another example, a sensor chip may comprise an array of electrodes that can electrostatically trap a carrier having a template nucleic acid at a plurality of the array positions. In another example, a template nucleic acid may be immobilized to a surface of a sensor or surface of array at an array position. Each array position may also comprise one or more electrodes capable of producing electric fields and/or functioning as sensors as described elsewhere herein. A template nucleic acid molecule associated with a carrier or immobilized to a sensor/array surface at an array position may be clonally amplified prior to sequencing, for example, with the aid of an electric field(s) generated by one or more of the electrodes at the array position. The electric field(s) can concentrate/isolate amplification reagents (e.g., primers, nucleotides, polymerase, etc.) to an array position. Following amplification, clonally amplified template nucleic acids can be subject to a nucleic acid sequencing reaction and sequenced as described elsewhere herein. Electrodes at an array position may also generate electric fields that can concentrate or isolate nucleic acid sequencing reaction reagents (e.g., sequencing primers, nucleotides, polymerase, etc.) to an array position.

Following the completion of amplification/sequencing reactions, carriers/nucleic acids may be dissociated from the array, the carriers and array optionally separated and washed, and either or both of the carriers and array subsequently re-used for another round of amplification and/or sequencing. Dissociation of a carrier from the array may be completed, for example, by removal/reversal of a magnetic and/or electric field used to hold the carrier in place. In addition or as an alternative, fluid flow and/or other type of field (e.g., external magnetic field, external electric field) capable of exerting forces sufficient for overcoming magnetic and/or electrostatic forces used to hold a carrier in place may also be used to dissociate the carrier from an array. Where nucleic acids are directly associated with the array or a sensor, in the absence of a carrier, the array or sensor may be treated with appropriate reagents or energy (e.g., enzymatic reagents, chemical reagents, thermal energy, etc.) to remove bound nucleic acids.

Figure 30A:
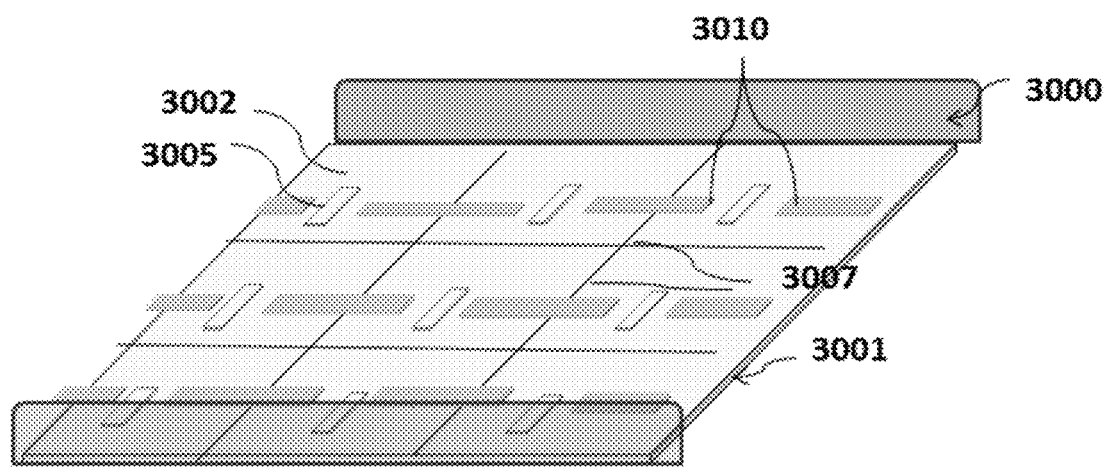
FIGS. 30A-30F schematically illustrate an example sensor chip and its use.

An example sensor chip is schematically depicted in FIGS. 30A-30F. As shown in FIG. 30A, the sensor chip 3000 may include a sensor array on a substrate 3001 that can comprise an array of sensor (e.g., nanosensors) positions 3002 that may be in fluid communication with microfluidic channels defined within the sensor chip 3000. As shown in FIG. 30A, the substrate 3001 can be configured as a substantially planar substrate. Each sensor position 3002 of the array may comprise magnetic 3010 and electrode 3005 and 3007 elements. Magnetic beads may be positioned at each sensor position 3002 by magnetic 3010 and/or electrode 3005 and 3007 elements. The magnetic elements 3010 may form localized magnetic fields and the electrode elements 3005 and 3007 may form localized electric fields in order to position a magnetic bead at each sensor position 3002 of the array. Moreover, the magnetic and/or electric fields may create an area of confinement that can be used to isolate and/or concentrate reagents at a sensor position 3002 of the array.

Figure 30B:
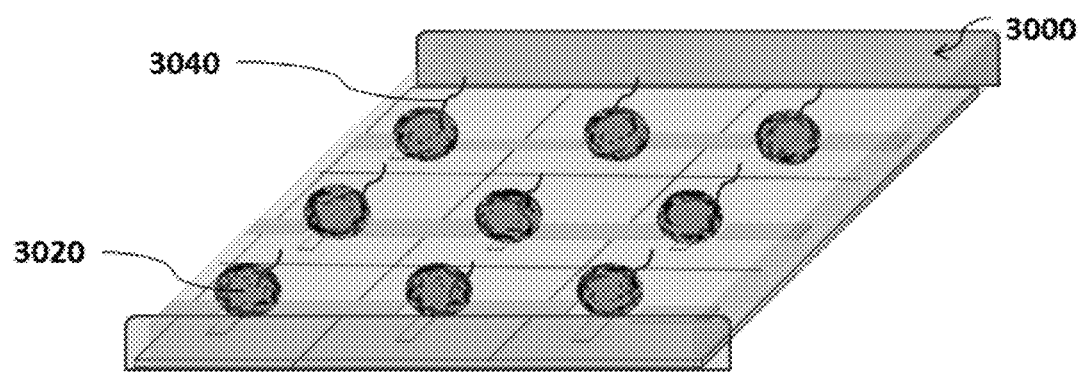

As shown in FIG. 30B, a sample comprising template nucleic acid 3040 (e.g., DNA, DNA fragments, RNA, RNA fragments) may be conveyed into the system 3000. In some cases, introduction of the template nucleic acid 3040 may be via microfluidic channels associated with the array, perhaps with the aid of microfluidic devices and valves described elsewhere herein. As shown in FIG. 30B, the array may comprise magnetic beads 3020 immobilized to the array via magnetic elements 3010 and/or electrode 3005 and 3007 elements. The magnetic beads 3020 may be associated with primers capable of hybridizing with template nucleic acid 3040, such that template nucleic acid 3040 is captured by and couples with the beads 3020. Other approaches may be used to couple the template nucleic acid 3040, such as covalent linkage, ionic interactions, dipole interactions, van der Waals forces, hydrophobic interactions, etc.

As an alternative, binding of template nucleic acid 3040 to magnetic beads 3020 can be performed separate from the sensor chip 3000 and the magnetic beads 3020 then provided via flow to the sensor chip 3000. Magnetic fields provided by magnetic elements 3010 and/or electrostatic interactions provided by electrodes 3005 and/or 3007 can capture magnetic beads 3020 as they are provided to the sensor chip 3000, such that they are each immobilized to a sensor position 3002 of the sensor chip 3000. Magnetic beads 3020 may be provided to the sensor chip via flow, perhaps with the aid of microfluidic valves and devices described elsewhere herein. Alternatively or in addition, primers may be bound, and/or associated with the array and used to capture nucleic acid 3040 on or near the array surface.

Figure 30C:
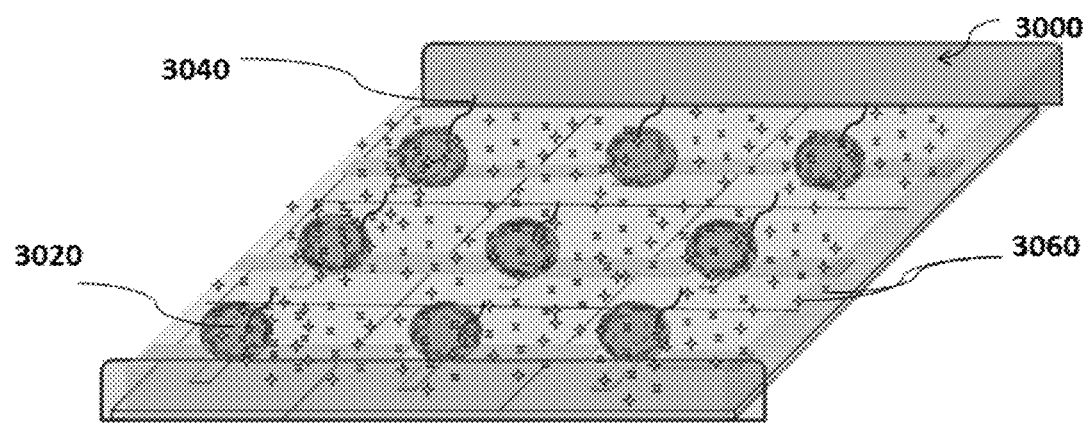

As shown in FIG. 30C, reagents 3060 (e.g., polymerase, deoxynucleoside triphosphates (dNTPs), and additional primers) may be simultaneously, previously, or subsequently introduced to the sensor chip 3000. In some cases, introduction of the reagents 3060 may be via flow through microfluidic channels associated with the sensor chip, such that the reagents 3060 are contacted with the magnetic beads 3020 via flow. Flowed reagents may be provided and/or removed from the sensor chip 3000 via microfluidic valves and devices described elsewhere herein. Via magnetic and/or electrostatic forces from the appropriate array elements, the magnetic beads 3020 are immobilized at sensor positions 3002 as reagents 3060 make contact with the magnetic beads 3020 via flow.

Figure 30D:
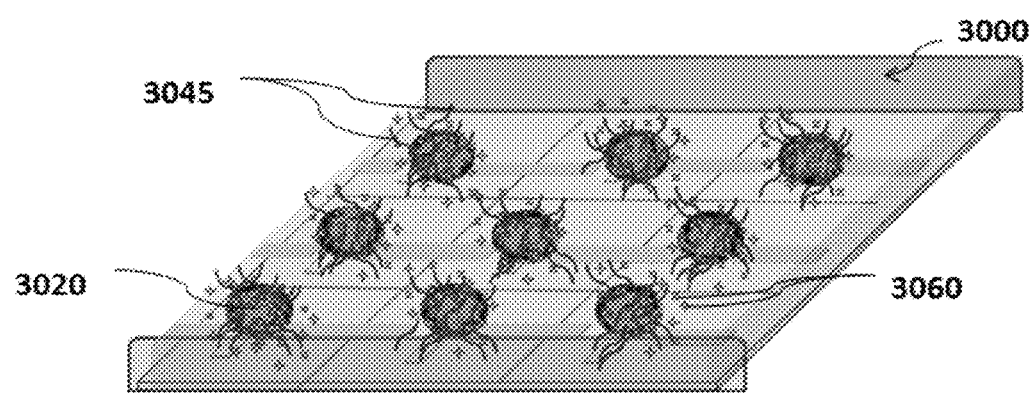

As shown in FIG. 30D, template nucleic acid 3040 associated with magnetic beads 3020 can be clonally amplified with the reagents 3060 and appropriate temperature conditions to produce amplified nucleic acid 3045 on the surface of the magnetic beads 3020. Clonal amplification may be completed using any suitable amplification method including a polymerase chain reaction (PCR), a primer extension reaction, isothermal amplification, or other techniques.

Figure 30E:
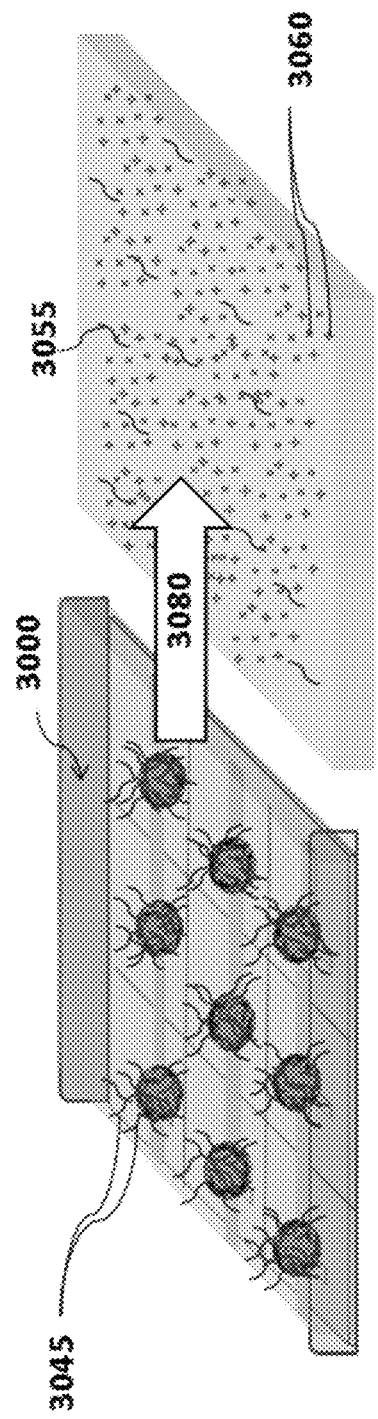

As shown in FIG. 30E, the magnetic beads 3020 may be washed 3080, removing unbound amplicons 3055 and reagents 3060 following amplification of template nucleic acid 3040. The washed magnetic beads 3020 comprise clonal sets of amplified nucleic acid 3045 associated with the sensor positions 3002. Washing 3080 may be completed by any suitable method, such as, for example, washing with a buffer solution at a flow rate sufficient to remove unbound amplicons 3055 and reagents 3060 in solution, but insufficient to jettison magnetic beads 3020 from their respective positions 3002 on the array. Washing fluids may be provided to the sensor chip via microfluidic valves and devices described elsewhere herein.

Figure 30F:
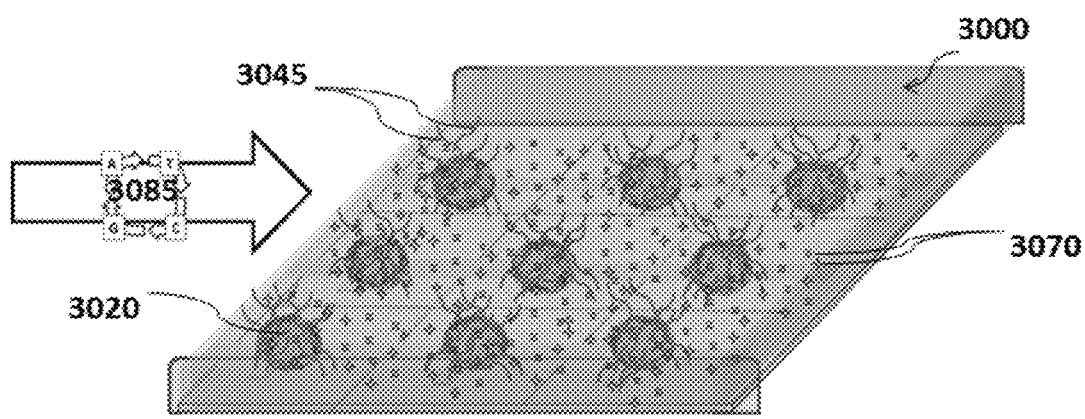

As shown in FIG. 30F, aliquots of reagents 3070 (e.g., polymerase, primers, dNTPs, etc.) may then be contacted (e.g., via flow) with the sensor array, whereby primers hybridize with amplified nucleic acids 3045 dNTPs are incorporated into the amplified nucleic acid 3045 of magnetic beads 3020 via the action of a polymerase. Aliquots of reagents 3070 each having a different dNTP (e.g., A, T, C or G) may be introduced in individual cycles, (e.g., cycle 1=A, cycle 2=T, etc). where there may be a wash step with buffer in between each cycle to help reduce the chance of contamination from unincorporated nucleotides. Polymerase used for the sequencing reaction, may be the same type of polymerase that is used for the amplification reaction, or may be a different type of polymerase, and can be introduced prior to or with introduction of the dNTPs. Sensors of the sensor chip 3000 can detect nucleotide incorporation events during each dNTP cycle, with signals obtained from the sensors used to sequence the amplified nucleic acid 3045, and, thus, the original template nucleic acid 3040.

Sensors may sense (e.g., detect signals indicative of) nucleotide incorporation events, for example, via one or both of electrodes 3005 and 3007. In some cases, electrodes 3005 and 3007 can sense nucleotide incorporation events by sensing a local impedance change, a local charge change, and/or a local conductivity change of the magnetic beads 3020 and/or the amplified nucleic acid (or other nucleic acid) 3045 associated with the magnetic beads 3020. Sensing can be achieved, for example, by directly measuring local impedance change or measuring a signal that is indicative of local impedance change. In some cases, a sensor may sense impedance within the Debye length (e.g., Debye layer) of the magnetic beads 3020 and/or the amplified nucleic acid 3045 associated with a magnetic bead 3020. Nucleotide incorporation events may also be sensed by directly measuring a local charge change or local conductivity change or a signal that is indicative of one or more of these. A sensor may sense a charge change or conductivity change within the Debye length (e.g., Debye layer) of a magnetic bead 3020 and/or amplified nucleic acid 3045 associated with the magnetic bead 3020.

In some cases, clonal amplification of template nucleic acid 3040 may be completed off the sensor chip 3000. In such cases, magnetic beads 3020 comprising clonally amplified nucleic acid 3045 can be provided to the sensor chip 3000 where magnetic fields provided by magnetic elements 3010 and or electric fields provided by electrodes 3005 and/or 3007 immobilize a magnetic bead 3020 at one or more the sensor positions 3002. Sequencing reactions and sensing of nucleotide incorporation events may then be completed on the amplified nucleic acid 3045 as described above.

Figure 23:
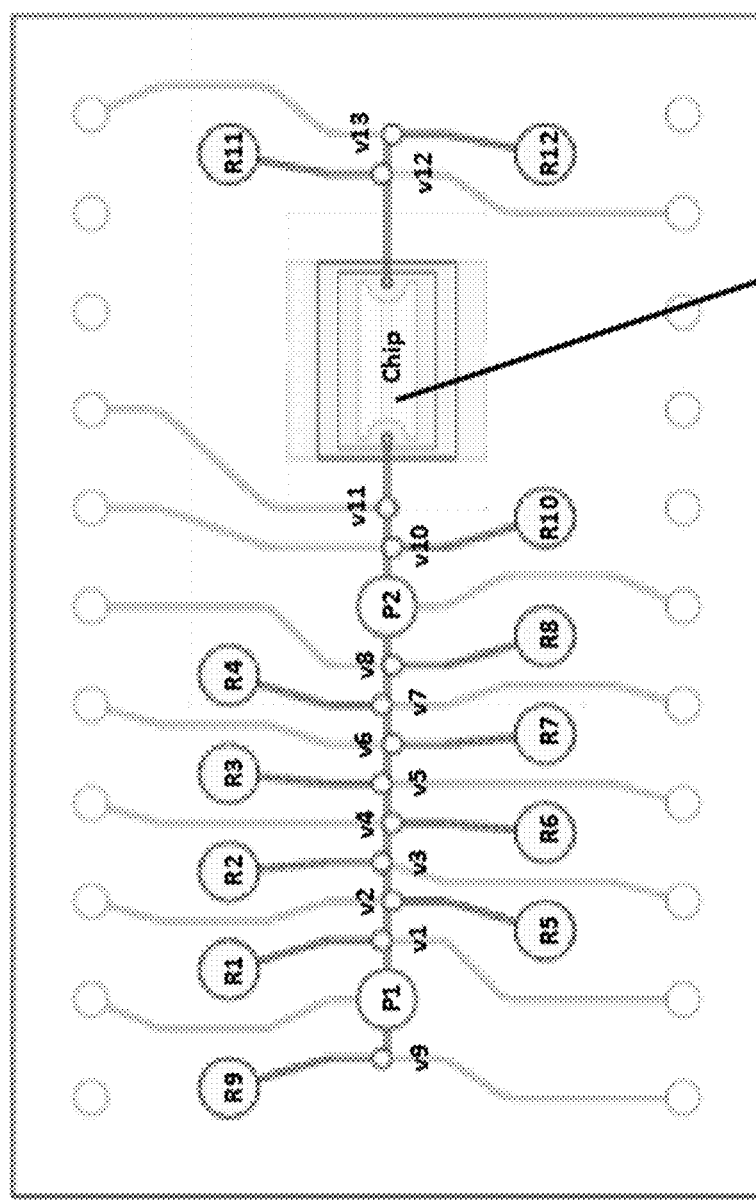
FIG. 23 schematically illustrates a top view of a DPM chip of the present disclosure integrated with a sensor chip.

FIG. 23 shows a top view of an example microfluidic DPM chip integrated with a sensor chip 2300, such as for example sensor chip 3000 described above. The DPM chip comprises twelve fluid reservoirs R1-R12, two pumps P1-P2 and thirteen valves v1-v13. The combined chip can flow the fluids from the reservoirs over the sensor chip in any order. In some cases (not shown), the DPM chip can be configured to perform mixing, nucleic acid amplification (e.g., PCR) or any other molecular biology operations needed to prepare a sample for sensing by the sensing chip.

Figure 24:
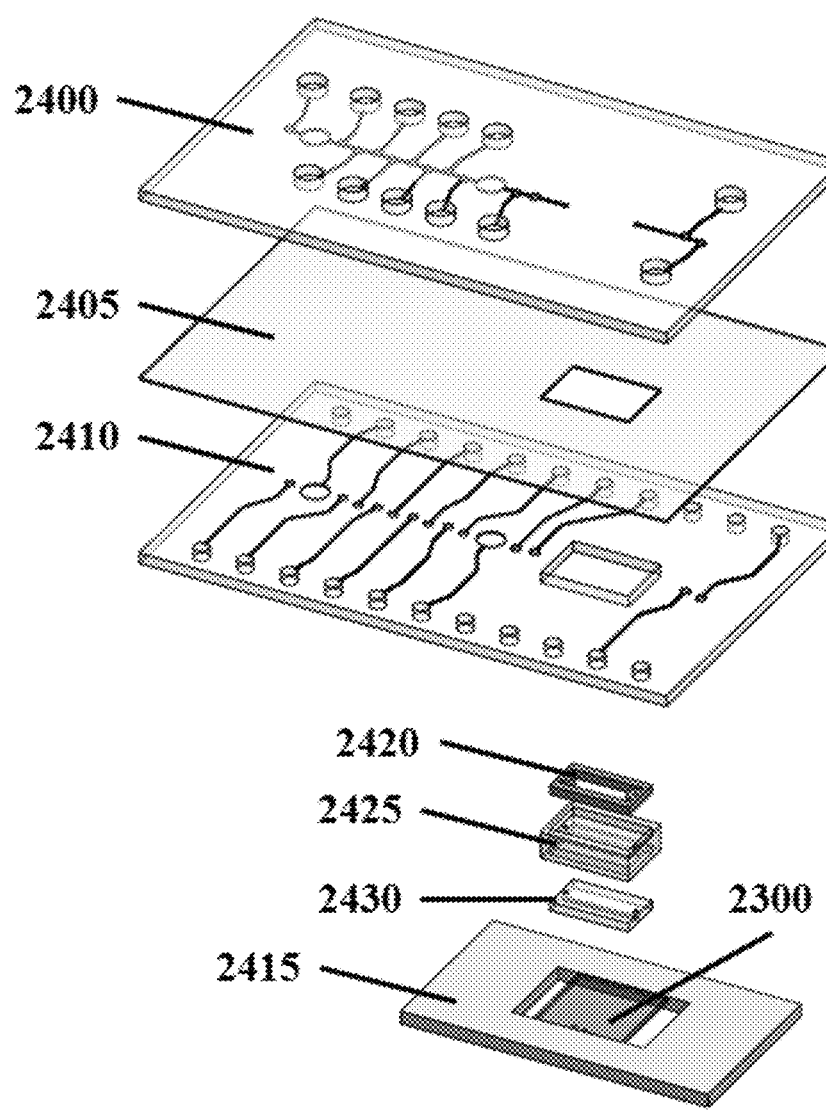
FIG. 24 schematically illustrates an exploded view of a DPM chip of the present disclosure integrated with a sensor chip.
Figure 25:
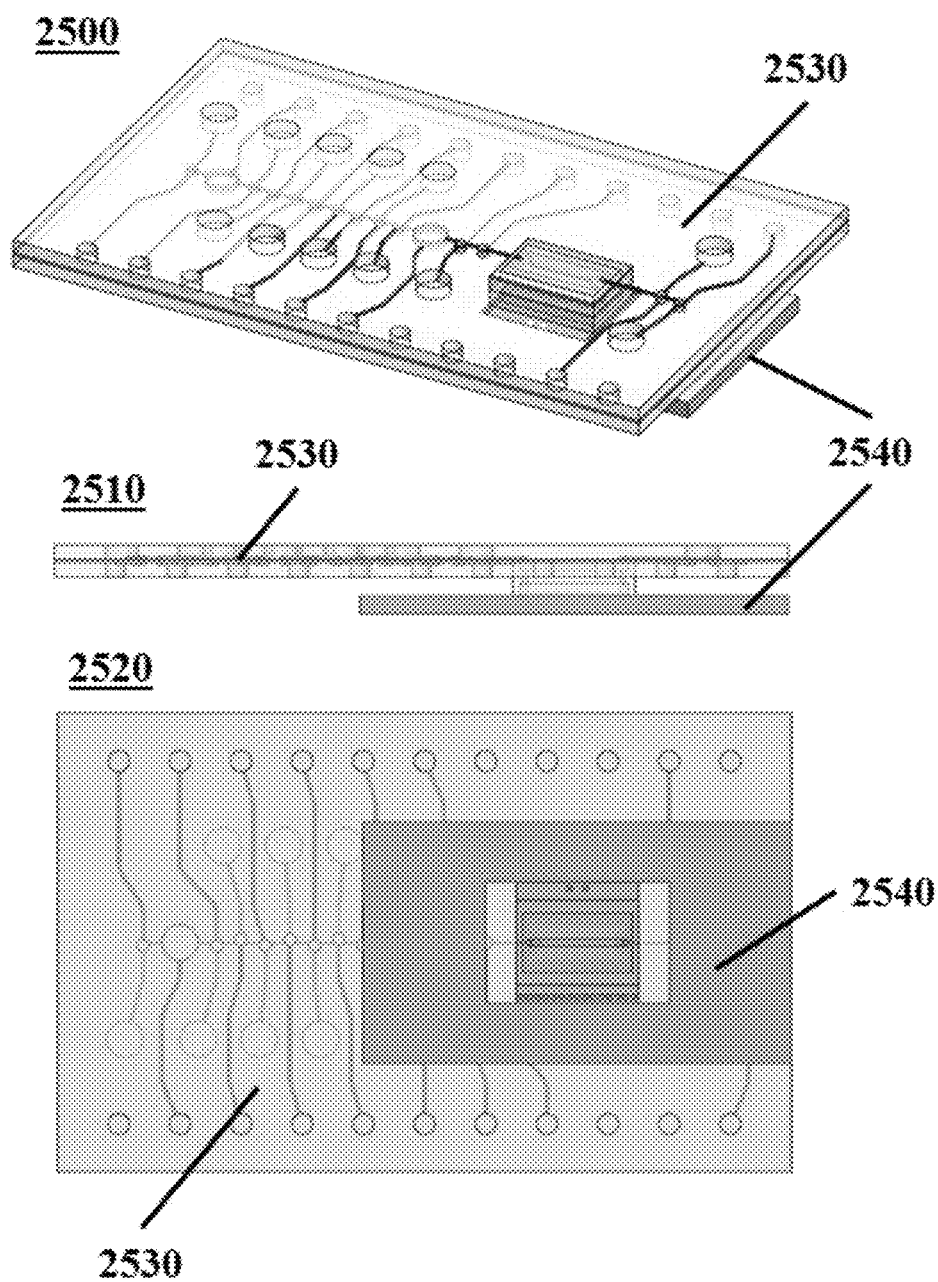
FIG. 25 schematically illustrates profile and bottom views of a DPM chip of the present disclosure integrated with a sensor chip.

With reference to FIG. 24, where like numerals represent like elements, the example DPM chip has a fluidic layer 2400, a film layer 2405 and a pneumatic layer 2410. The DPM chip is integrated with the sensor chip assembly 2415 through a fluidic interface gasket 2420, an interface block 2425 and a chip interface gasket 2430. Additional views of the assembled system are shown in FIG. 25, including an abstract view 2500, a profile view 2510 and a bottom view 2520, where the DPM chip 2530 and sensor chip assembly 2540 are shown.

Control Systems

Figure 26:
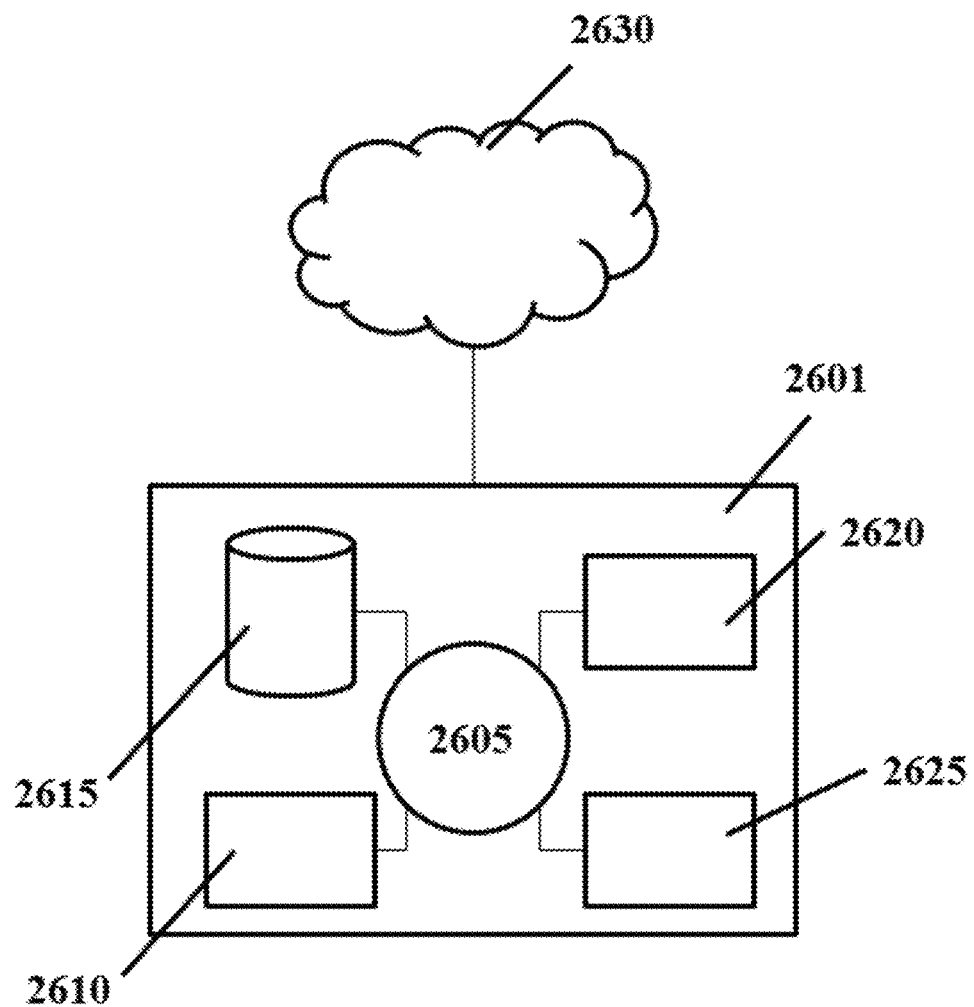
FIG. 26 schematically illustrates a computer system that is programmed or otherwise adapted to implements the methods of the disclosure.

The present disclosure provides computer control systems that are programmed or otherwise configured to implement methods and systems of the present disclosure. FIG. 26 shows a computer system 2601 that is programmed or otherwise configured to regulate sample processing and/or analysis using microfluidic devices and systems provided herein. The computer system 2601 can regulate various aspects of sample processing, such as, for example, heat flow (e.g., heating or cooling), fluid flow, fluid mixing, fluid separation and reaction (e.g., nucleic acid amplification).

The computer system 2601 includes a central processing unit (CPU, also "processor" and "computer processor" herein) 2605, which can be a single core or multi core processor, or a plurality of processors for parallel processing. The computer system 2601 also includes memory or memory location 2610 (e.g., random-access memory, read-only memory, flash memory), electronic storage unit 2615 (e.g., hard disk), communication interface 2620 (e.g., network adapter) for communicating with one or more other systems, and peripheral devices 2625, such as cache, other memory, data storage and/or electronic display adapters. The memory 2610, storage unit 2615, interface 2620 and peripheral devices 2625 are in communication with the CPU 2605 through a communication bus (solid lines), such as a motherboard. The storage unit 2615 can be a data storage unit (or data repository) for storing data. The computer system 2601 can be operatively coupled to a computer network ("network") 2630 with the aid of the communication interface 2620. The network 2630 can be the Internet, an internet and/or extranet, or an intranet and/or extranet that is in communication with the Internet. The network 2630 in some cases is a telecommunication and/or data network. The network 2630 can include one or more computer servers, which can enable distributed computing, such as cloud computing. The network 2630, in some cases with the aid of the computer system 2601, can implement a peer-to-peer network, which may enable devices coupled to the computer system 2601 to behave as a client or a server.

The CPU 2605 can execute a sequence of machine-readable instructions, which can be embodied in a program or software. The instructions may be stored in a memory location, such as the memory 2610. Examples of operations performed by the CPU 2605 can include fetch, decode, execute, and writeback.

The storage unit 2615 can store files, such as drivers, libraries and saved programs. The storage unit 2615 can store programs generated by users and recorded sessions, as well as output(s) associated with the programs. The storage unit 2615 can store user data, e.g., user preferences and user programs. The computer system 2601 in some cases can include one or more additional data storage units that are external to the computer system 2601, such as located on a remote server that is in communication with the computer system 2601 through an intranet or the Internet.

The computer system 2601 can communicate with one or more remote computer systems through the network 2630. For instance, the computer system 2601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2601 via the network 2630.

Methods as described herein can be implemented by way of machine (e.g., computer processor) executable code stored on an electronic storage location of the computer system 2601, such as, for example, on the memory 2610 or electronic storage unit 2615. The machine executable or machine readable code can be provided in the form of software. During use, the code can be executed by the processor 2605. In some cases, the code can be retrieved from the storage unit 2615 and stored on the memory 2610 for ready access by the processor 2605. In some situations, the electronic storage unit 2615 can be precluded, and machine-executable instructions are stored on memory 2610.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

Example 1

Reaction Mixing and Incubation

Figure 27:
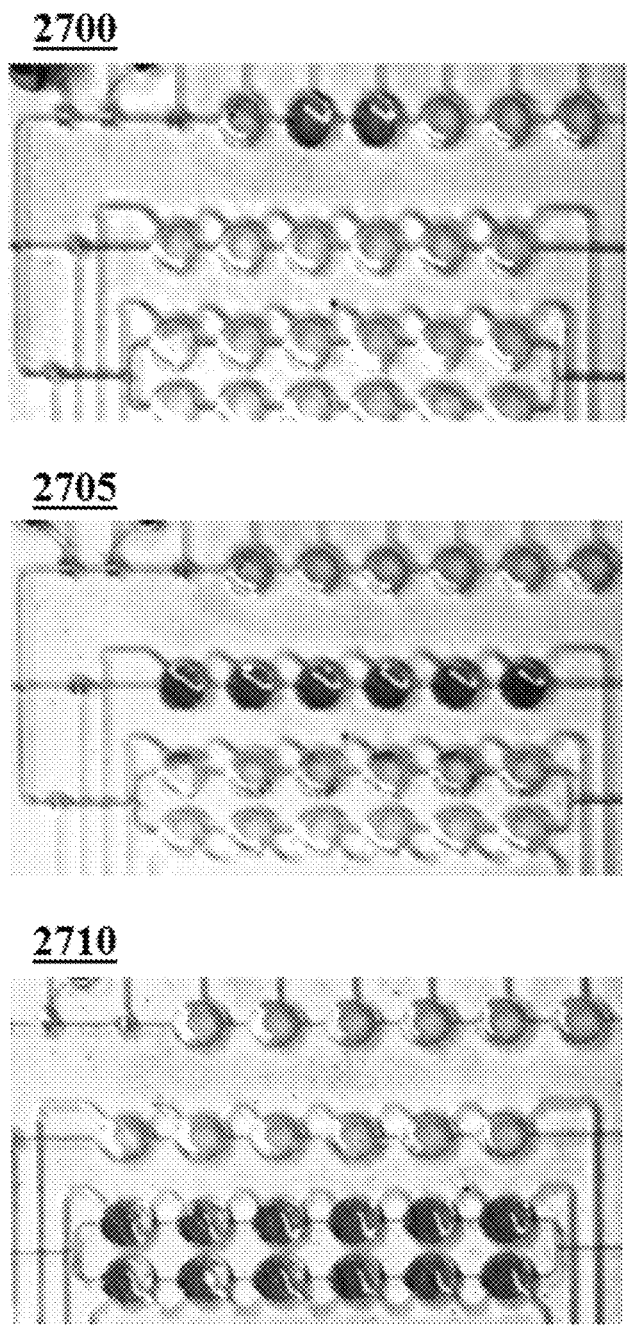
FIG. 27 shows an example of sample mixing in a DPM chip of the present disclosure.

FIG. 27 shows results of reaction volume mixing. Solutions having yellow or blue food dye were placed in wells as shown in FIG. 16 (with yellow being light gray and blue being dark gray as they appear in FIG. 16). Typical results for single volume mixing are shown 2700. In this experiment, blue and yellow food dye in reservoirs L2 and S1 were primed and introduced into P1 and P0, respectively, and then mixed as described above. The results of six volume mixing 2705 (six pump volumes have been reciprocally transferred between [P0-P5] and P6) and Twelve Volume mixing 2710 (twelve pump volumes have been reciprocally transferred between [P0-P5]+P6 and P7) are also shown in FIG. 27. In each case, the mixed volumes are approximately the same color, an indication of good mixing.

Chip chemical compatibility was confirmed with an RPA (recombinase polymerase amplification) reaction. The RPA reaction-Mg was placed in reservoir LR2 and $Mg^{++}$ was placed in reservoir S1. The two components were mixed 1:1 and incubated in the chip for 10 minutes. The product was pumped to reservoir P and recovered. Double-stranded DNA content was determined with a fluorescent assay. The results indicate that an RPA amplification reaction mixed and incubated for ten minutes in the chip performed at approximately the same level as a reaction performed conventionally in microtubes (368 ng/µL for the microfluidic reaction versus 434 ng/µL for the microtubes).

Example 2

Magnetic Beads Processing and DNA Purification

Figure 28:
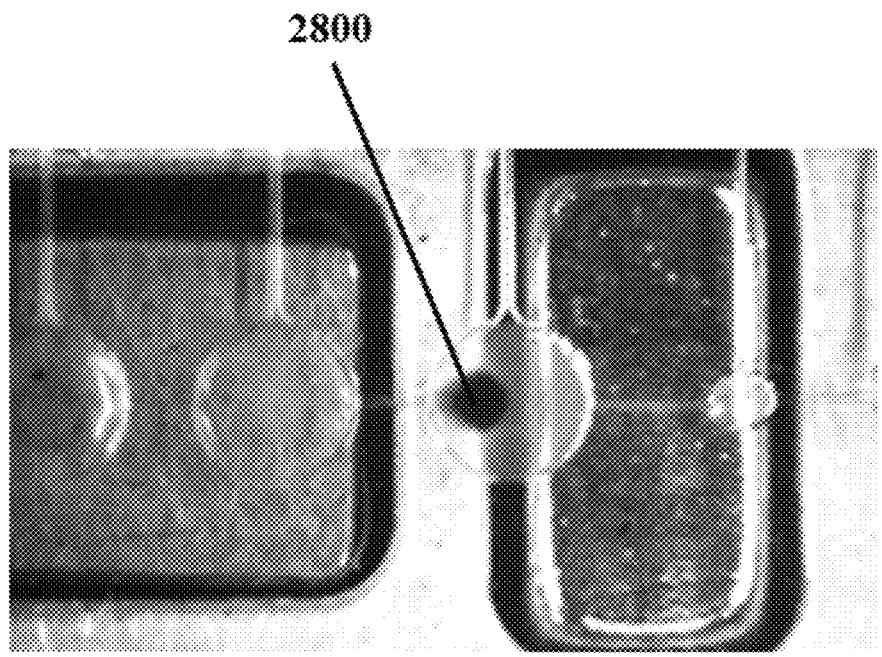
FIG. 28 shows an example of magnetic bead capture in a DPM chip of the present disclosure.

As shown in FIG. 28 and with respect to the example device shown in FIG. 14, superparamagnetic beads 2800 (Seradyne Speedbeads, 1 µm double-shelled superparamagnetic polymer beads) can be captured in pump P5 by a high-strength magnet positioned beneath the chip. Bead capture involves the sequential pumping of a bead binding reaction from left to right through P5 to a waste reservoir in the Right I/O Rail with the external magnet under P5 in the raised position. Efficient bead capture is facilitated by the (computer-controlled) insertion of air flow restrictors in the pneumatic control lines connected to pumps P4 or P5. For example, pump P4's flow restrictor slows P4's membrane transition from open to closed states as P4's control line is switched from vacuum to positive pressure. This reduction in pump membrane velocity results in a reduction in linear fluid velocity through P5, reducing hydrodynamic drag on the beads in P5 and allowing more time for bead capture. Once captured in P5, beads may be washed and dried in a similar manner, by pumping a wash buffer (e.g., 70-90% EtOH), and then air, through P5 to waste. Captured nucleic acids may be eluted from the washed and dried beads by filling P5 with elution buffer (e.g., TE), and, optionally, breaking up the captured bead "pellet" by reciprocal pumping between P4 and P5 with the magnet down. The eluted beads may then be recaptured in P5 and the eluate (containing nucleic acids) may be pumped either to the product output reservoir (P) or back into P4 for further processing. Implementations of the above described process (e.g., bead capture, washing, drying, and elution) were approximately 80% as efficient as bench reference experiments using initially bead-bound lambda phage DNA and a 7% PEG8000, 2.5M NaCl bead binding solution with Seradyne Speedbeads.

Example 3

Temperature-Control and Thermocycling

As described herein and with respect to the example device shown in FIG. 14, both top and bottom surfaces of the P0-P4 region of the a main processor can be heated to provide either constant temperature (isothermal) incubation or thermocycling of reactions assembled in these pumps. FIG. 29 shows PCR thermocycling temperature profiles for an example system, including internal chip temperatures monitored by a thermocouple positioned between P2 and P3 on the fluidic side of the chip film. Traces are shown for the bottom heater set point, top heater set point, bottom heater thermocouple, top heater thermocouple, and internal chip thermocouple, each of which shows temperature changes on a similar time scale. These results show that the rise and fall times for 60° C. to 95° C. transitions are both approximately 40 seconds. Cooling in the system is passive, as the bulk of the bottom surface of the chip is clamped tightly to the relatively massive room temperature aluminum base manifold. No delamination or distortion of chip structure was observed over 40 PCR cycles, confirming that COP-TPE bonding is stable during thermocycling.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A microfluidic device, comprising:
 a first channel having a sequence of (n) chambers each having a first volume (v), wherein said first channel comprises valves at opposing ends of said first channel that fluidically isolate said first channel; and
 a second channel in fluid communication with said first channel, wherein said second channel includes at least one second chamber having a total second volume that is at least equal to said total volume of said first channel (n*v), wherein said second channel comprises valves at opposing ends of said second channel that fluidically isolate said second channel from said first channel; and
 at least a fluidic layer, an actuation layer, and an elastic layer sandwiched between said fluidic layer and said actuation layer,
 wherein at least one of said valves comprises:
 a) a diaphragm in said elastic layer;
 b) a valve seat that selectively isolates an inlet and an outlet of said at least one of said valves;
 c) a chamber in said actuation layer, which chamber supplies positive or negative fluidic or pneumatic pressure to move said diaphragm towards or away from said valve seat, and
 d) a pin that is movable within said chamber relative to said diaphragm, wherein said diaphragm is movable towards said valve seat using positive pressure at least partly supplied by said pin.

2. The microfluidic device of claim 1, further comprising a third channel in fluid communication with said first channel and said second channel, wherein said third channel includes at least one third chamber having a total third volume that is at least equal to a sum of said first and second channel volumes (2n*v).

3. The microfluidic device of claim 1, wherein said elastic layer is substantially free of polydimethylsiloxane.

4. A microfluidic device, comprising:
 a first channel having a sequence of (n) chambers each having a first volume (v), wherein said first channel comprises valves at opposing ends of said first channel that fluidically isolate said first channel; and
 a second channel in fluid communication with said first channel, wherein said second channel includes at least one second chamber having a total second volume that is at least equal to said total volume of said first channel (n*v), wherein said second channel comprises valves at opposing ends of said second channel that fluidically isolate said second channel from said first channel; and
 at least a fluidic layer, an actuation layer, and an elastic layer sandwiched between said fluidic layer and said actuation layer,
 wherein at least one of said chambers comprises:
 a) a diaphragm in said elastic layer;
 b) a fluid chamber in said fluidic layer; and
 c) a chamber in said actuation layer, which chamber supplies positive or negative fluidic or pneumatic pressure to deform said diaphragm to effect fluid flow or mixing in fluid chamber, and
 d) a pin that is movable within said chamber relative to said diaphragm, wherein said diaphragm is movable using positive pressure at least partly supplied by said pin.

5. The microfluidic device of claim 1, wherein (i) a first subset of said n chambers in said first channel is in thermal communication with a first temperature zone and (ii) a second subset of said n chambers in said first channel is in thermal communication with a second temperature zone.

6. The microfluidic device of claim 1, wherein n is equal to at least 3.

* * * * *